US012133881B2

(12) United States Patent
Schmidt et al.

(10) Patent No.: US 12,133,881 B2
(45) Date of Patent: Nov. 5, 2024

(54) ELECTRICAL STIMULATION OF CELLS TO INDUCE ENHANCED SECRETOME FOR THERAPEUTIC APPLICATIONS

(71) Applicant: University of Florida Research Foundation, Inc., Gainesville, FL (US)

(72) Inventors: Christine E. Schmidt, Gainesville, FL (US); Sahba Mobini, Tres Cantos Madrid (ES)

(73) Assignee: University of Florida Research Foundation, Inc., Gainesville, FL (US)

( * ) Notice: Subject to any disclaimer, the term of this patent is extended or adjusted under 35 U.S.C. 154(b) by 722 days.

(21) Appl. No.: 17/263,263

(22) PCT Filed: Aug. 1, 2019

(86) PCT No.: PCT/US2019/044731
§ 371 (c)(1),
(2) Date: Jan. 26, 2021

(87) PCT Pub. No.: WO2020/028708
PCT Pub. Date: Feb. 6, 2020

(65) Prior Publication Data
US 2021/0187070 A1 Jun. 24, 2021

Related U.S. Application Data

(60) Provisional application No. 62/746,280, filed on Oct. 16, 2018, provisional application No. 62/713,218, filed on Aug. 1, 2018.

(51) Int. Cl.
| | | |
|---|---|---|
| A61K 38/18 | (2006.01) | |
| A61K 9/00 | (2006.01) | |
| A61K 9/06 | (2006.01) | |
| A61K 35/28 | (2015.01) | |
| A61K 35/32 | (2015.01) | |
| A61K 35/34 | (2015.01) | |
| A61K 35/44 | (2015.01) | |
| C12N 5/071 | (2010.01) | |
| C12N 5/077 | (2010.01) | |
| C12N 5/0775 | (2010.01) | |
| C12N 13/00 | (2006.01) | |

(52) U.S. Cl.
CPC ............ *A61K 38/18* (2013.01); *A61K 9/0019* (2013.01); *A61K 9/06* (2013.01); *A61K 35/28* (2013.01); *A61K 35/32* (2013.01); *A61K 35/34* (2013.01); *A61K 35/44* (2013.01); *C12N 5/0655* (2013.01); *C12N 5/0657* (2013.01); *C12N 5/0667* (2013.01); *C12N 5/069* (2013.01); *C12N 13/00* (2013.01)

(58) Field of Classification Search
None
See application file for complete search history.

(56) References Cited

FOREIGN PATENT DOCUMENTS

WO 2017139795 A1 8/2017

OTHER PUBLICATIONS

International Search Report issued for PCT/US2019/044731, mailed Dec. 3, 2019.
Pavesi et al., Electrical conditional of adipose-derived stem cells in a multi-chamber culture platform, Biotechnology and Bioengineering, vol. 111, No. 7, p. 1452-1463, 2014.
Martins et al., Mesenchymal Stem Cells Secretome-Induced Axonal Outgrowth is mediated by BDNF, Scientific Reports, vol. 7, No. 1, p. 1-13, 2017.
Campbell et al., Electrical Stimulation to Optimize Cardioprotective Exosomes from Cardiac Stem Cells, Medical Hypotheses, vol. 88, p. 6-9, 2016.
Evers-van Gogh et al., Electric Pulse Stimulation of Myotubes as an In Vitro Exercise Model: Cell-Mediated and Non-Cell-Mediated Effects, Nature, Scientific Reports, 5:10944, p. 1-11, 2005.
Huang et al., Electrical regulation of Schwann cells using conductive polypyrrole/chitosan polymers, Electrical Regulation of Schwann Cells Using Conductive Polymers, 164-174, 2009.
Hwang et al., The Implications of the Response of Human Mesenchymal Stromal Cells in Three-Dimensional Culture to Electrical Stimulation for Tissue Regeneration, Tissue Engineering: Part A, vol. 18, No. 3 and 4, 432-445, 2012.
Kim et al., Novel Effect of Biphasic Electric Current on In Vitro Osteogenesis and Cytokine Production in Human Mesenchymal Stromal Cells, Tissue Engineering: Part A, vol. 15, 2411-2422, 2009.
Koppes et al., Electrical Stimulation of Schwann Cells Promotes Sustained Increases in Neurite Outgrowth, Tissue Engineering: Part A, vol. 20, No. 3 and 4, 494-506, 2014.

(Continued)

*Primary Examiner* — Michael V Meller
(74) *Attorney, Agent, or Firm* — Thomas|Horstemeyer, LLP

(57) ABSTRACT

Disclosed herein is a method of treating a subject for a disease, disorder, or condition that involves administering to the subject a composition comprising a secretome derived from electrically stimulated cells. Also disclosed herein is an enhanced secretome produced by a process comprising collecting cells from a subject, culturing the cells in a serum free medium for at least 1 day while stimulating the cells with electric pulses, and collecting the secretome produced by the electrically-stimulated cells. Also disclosed herein is a pharmaceutical composition comprising an enhanced secretome derived from electrically stimulated cells contained within a biocompatible hydrogel in an amount effective to treat a disease or disorder.

7 Claims, 25 Drawing Sheets

(56) References Cited

OTHER PUBLICATIONS

Scheler et al., Methods for Proteomics-Based Analysis of the Human Muscle Secretome Using an In Vitro Exercise Model, Anton Posch (ed.), Proteomic Profiling: Methods and Protocols, Methods in Molecular Biology, vol. 1295, 55-64, 2005.
Wei et al., IFATS Collection: The Conditioned Media of Adipose Stromal Cells Protect Against Hypoxia-Ischemia-Induce Brain Damage in Neonatal Rats, Stem Cells, 27:478-488, 2009.

ELECTRICAL STIMULATION OF CELLS TO INDUCE ENHANCED SECRETOME FOR THERAPEUTIC APPLICATIONS

CROSS-REFERENCE TO RELATED APPLICATIONS

This application is a National Stage of International Application No. PCT/US2019/044731, filed Aug. 1, 2019, which claims benefit of U.S. Provisional Application No. 62/746,280, filed Oct. 16, 2018, and U.S. Provisional Application No. 62/713,218, filed Aug. 1, 2018, which is hereby incorporated herein by reference in its entirety.

BACKGROUND

The current therapy of transplantation of intact organs and tissues to treat organ and tissue failures and loss suffers from limited donor supply and often severe immune complications, but these obstacles may potentially be bypassed through the use of regenerative medicine strategies. The field of regenerative medicine encompasses numerous strategies, including the use of materials and de novo generated cells, as well as various combinations thereof, to take the place of missing tissue, effectively replacing it both structurally and functionally, or to contribute to tissue healing. The body's innate healing response may also be leveraged to promote regeneration, although adult humans possess limited regenerative capacity in comparison with lower vertebrates.

SUMMARY

The secretome is the totality of secreted organic molecules and inorganic elements by biological cells, tissues, organs, and organisms. The disclosed compositions and methods harness the power of these secreted factors (or the secretome of cells), which include growth factors, cytokines, and extracellular vesicles, for tissue regeneration. Using the secretions of cells as the main therapeutic, rather than the cells themselves (cell-free approach), avoids possible immunogenic responses from the recipient. In addition, endogenous electrical field (EF) in the injured tissue (injury potential) of damaged tissue promotes natural tissue regeneration. Delivering electrical stimulation (E-stim) similar to the endogenous EF, showed to improve healing process. However, delivering E-stim to the tissue, in a minimally invasive way, remains a challenge and the direct mechanisms by which electrical stimulation induces regeneration is unclear. As disclosed herein, electrical stimulation of cells ex vivo can be used to produce an enhanced secretome for many therapeutic applications, including but not limited to tissue engineering and regenerative medicine applications (e.g., treatment of myocardial infarction, spinal cord injury treatment, bone and cartilage regeneration, and other regenerative tissue systems). This allows for application of the known benefits of electrical stimulation on cells indirectly, thus noninvasively, to the damaged tissues. Electrical stimulation also provides scalable techniques and a control mechanism to tune the secretome for several regenerative medicine applications Therefore, disclosed herein is a method of treating a subject for a disease, disorder, or condition that involves administering to the subject a composition comprising a secretome derived from electrically stimulated cells in an amount effective to treat the disease, disorder, or condition. In some embodiments, the cells are autologous cells isolated from the subject to be treated. In some embodiments, the cells are donor cells, cell lines, or banked cells.

Many different diseases, disorders, or conditions can be treated by the disclosed compositions and methods. For example, in some embodiments, the disease, disorder, or condition is spinal cord injury or defects. As an example, in these embodiments the cells can be mesenchymal stem/stromal cells (MSCs) (e.g. derived from fat, bone marrow, or umbilical cord), induced pluripotent stem cells (iPSCs), neural stem cells, Schwann cells, or any combination thereof.

In some embodiments, the disease, disorder, or condition is traumatic brain injury. As an example, in these embodiments the cells can be iPSCs, neural stem cells, astrocytes, or any combination thereof.

In some embodiments, the disease, disorder, or condition is non-union bone fractures, delayed union bone fractures, or a combination thereof. As an example, in these embodiments the cells can be MSCs (e.g. derived from fat, bone marrow, or umbilical cord).

In some embodiments, the method involves peripheral nerve regeneration. As an example, in these embodiments the cells can be Schwann cells, neural stem cells, or any combination thereof.

In some embodiments, the disease, disorder, or condition is myocardial infarction. As an example, in these embodiments the cells can be iPSCs, cardiomyocytes, or any combination thereof.

In some embodiments, the disease, disorder, or condition is a diabetic ulcer. As an example, in these embodiments the cells can be MSCs (e.g. derived from fat, bone marrow, or umbilical cord), fibroblast, endothelial cells, or any combination thereof.

Also disclosed herein is an enhanced secretome produced by a process comprising collecting cells from a subject, culturing the cells in a serum free medium for at least 1 day while stimulating the cells with electric pulses (the regime of electrical stimulation can be changed for each specific target), and collecting the secretome produced by the electrically-stimulated cells. In some embodiments, the obtained secretome is formulated in a hydrogel for administration to the subject.

Also disclosed herein is a pharmaceutical composition comprising an enhanced secretome derived from electrically stimulated cells contained within a biocompatible hydrogel in an amount effective to treat a disease, disorder, or condition.

As disclosed herein, using the secretions of cells (which is improved by electrical stimulation) as the main therapeutic, rather than the cells themselves, avoids possible immunogenic responses from the recipient. In addition, the secretome can be concentrated and purified to deliver high concentrations in minimal volume, further reducing invasiveness and risks (compared to, for example, large injections of cells in cell-based therapies). It is expected that the shelf-life of the secretome is longer than for cell therapies, minimizing time needed for preparation and implementation. Moreover, secretome has less regulatory burden than cell therapy. Interestingly, local electrical stimulation of damaged tissue after injury has been shown to promote tissue regeneration.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 13B to 13E show effect of secretome on number of junctions (FIG. 13B), number of meshes (FIG. 13C), number of nodes (FIG. 13D), and total tubule length (FIG. 13E).

FIGS. 15B and 15C show DRG neurite outgrowth area after 2 days (FIG. 15B) and normalized DRG neurite outgrowth area after 2 days (FIG. 15C).

DETAILED DESCRIPTION

Figure 1:
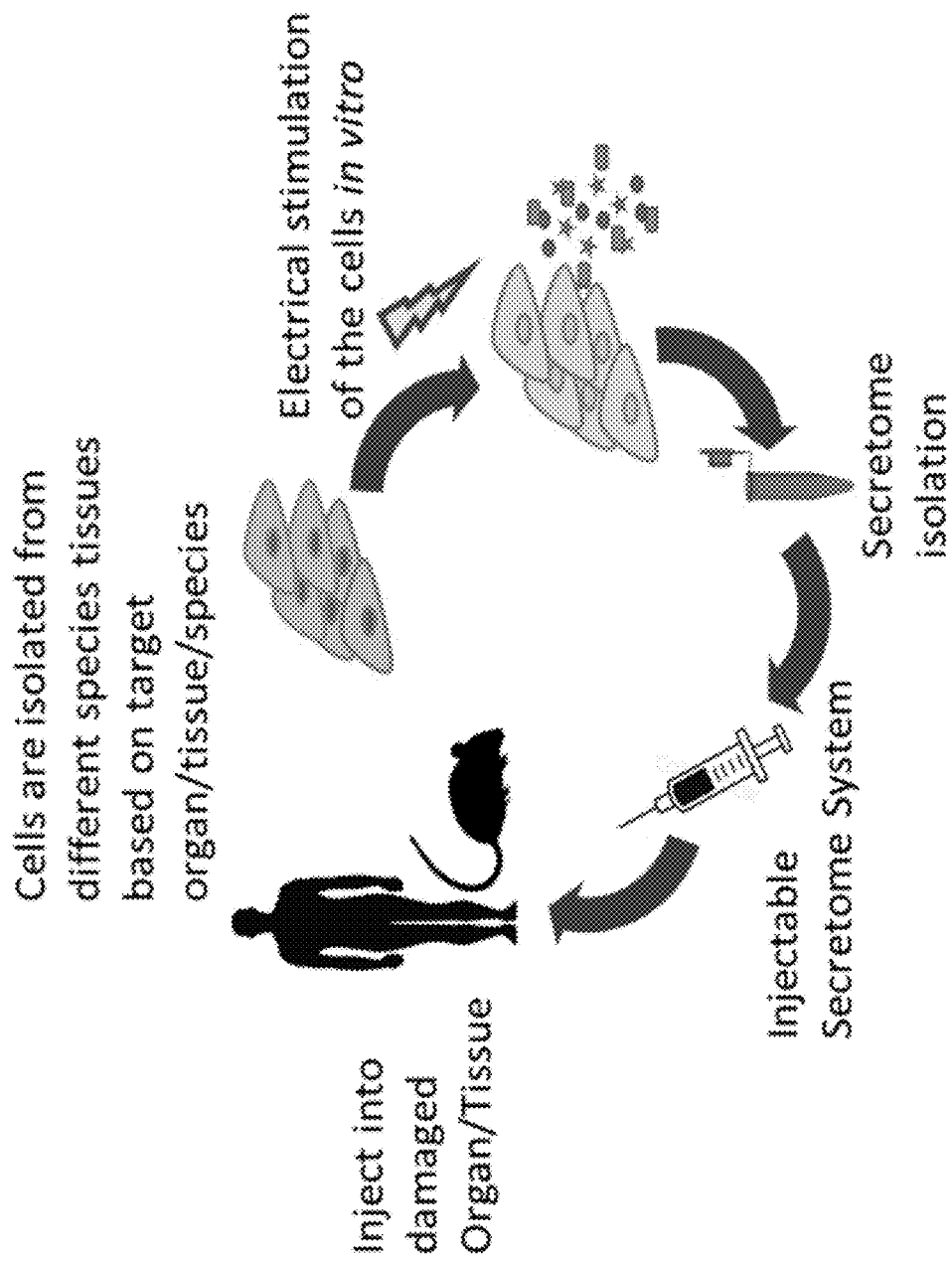
FIG. 1 is a schematic showing electrical stimulation used to produce a secretome for tissue engineering and regenerative medicine application.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

Definitions

The term "secretome" as used herein refers to all of the factors secreted by a cell. This includes proteins, such as growth factors, chemokines, cytokines, adhesion molecules, proteases and shed receptors. In addition to the protein cargo, non-protein components, such as lipid, micro-RNAs and messenger-RNA, could also be secreted by cells via both microvesicles and exosomes.

The term "enhanced secretome" as used herein refers to the secretome of an electrically stimulated cell.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Cells

In some embodiments, the disclosed secretomes can be produced from any cell type. It will be understood that the choice of cell type is dependent upon the disease, disorder, or condition to be treated. For example, cardiomyocytes are useful for producing a secretome that can treat diseases, disorders, and/or conditions of the heart.

In some cases, the cells are stem cells or progenitor cells. In some embodiments, the cells have been differentiated ex vivo from stem cells or progenitor cells. Examples of stem cells found in adult tissues include hematopoietic stem cells, mammary stem cells, intestinal stem cells, mesenchymal stem cells, endothelial stem cells, neural stem cells, olfactory adult stem cells, neural crest stem cells, and testicular cells. Sources for adult stem cells include bone marrow, skin tissue, and adipose tissue.

In some embodiments, the cells are primary cells obtained from a subject. In particular embodiments, the cells can be autologous or allogenic. In some embodiments, the cells have been subjected to multiple passages for expansion and storage. In some embodiments, the cells are immortalized as a cell line.

Electrical Stimulation

Cells can be electrically stimulated during cell culture in 2D and 3D platforms by incorporating anodes and cathodes into the culture chamber. The cells are preferably cultured in a serum free medium at physiological temperatures and atmosphere. The choice of medium and other additives and parameters can be selected and optimized based on the cell type.

The cells can be stimulated to produce enhanced secretomes using electric pulses at a frequency of from about 1 µHz to about 10 kHz. The optimal frequency highly depends on target tissue. For example, for SCI, 1 kHz may work better, whereas for bone, a frequency in the µHz range (DC) is likely optimal.

In some embodiments the electrical field ranges from 0.1 V/mm to 150 V/mm. For example, in some preferred embodiments, the electrical field ranges from about 10 V/m to about 100 V/m, including from about 20 to about 50 V/m.

In some embodiments the signal shape can be either a sine or pulse. In some preferred embodiments, the signal is a pulse field.

The duration of the electrical field can range from about 0.5 hours to about 8 hours per day for 1 to 7 days. In some preferred embodiments, the duration is about 1 hour per day for 1 to 7 days, including about 1 hour per day for 3 days.

Secretomes

The secretome can be obtained by collecting the medium conditioned during the electrical stimulation. The dead cells and debris are preferably removed by centrifugation (e.g. 300×g for 4 minute). In some embodiments, the medium is dried (e.g. by lyophilization) prior to being re-suspended in a pharmaceutically acceptable excipient. The soluble components of the secretome can be separated from the microvesicle fraction by centrifugation, filtration, polymer precipitation-based methodologies, ion exchange chromatography or size-exclusion chromatography.

The secretomes may be analyzed by known methods, such as Western blotting, enzyme-linked immunosorbent assay, as well as (mass spectrometry-based) proteomics approaches as described in the literature, and includes determining the expression profile of miRNA regulating gene expression at the posttranscriptional level and mRNA as regenerative messengers at cell signaling level.

Pharmaceutical Compositions

Disclosed is a pharmaceutical compositions containing therapeutically effective amounts of an enhanced secretome produced according to the methods disclosed herein and a pharmaceutically acceptable carrier. Pharmaceutical carriers suitable for administration of the compounds provided herein include any such carriers known to those skilled in the art to be suitable for the particular mode of administration.

In some embodiments, the compositions are formulated for single dosage administration. To formulate a composition, the enhanced secretome is dissolved, suspended, dispersed or otherwise mixed in a selected carrier at an effective amount and concentration such that the treated condition is relieved or one or more symptoms are ameliorated.

The electrically enhanced secretomes described herein can be formulated as an injectable for parenteral administration. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (See, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxy ethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

The electrically enhanced secretomes described herein can be formulated in a hydrogels that mimic tissue extracellular matrix (ECM). Examples of ECM-mimicking hydrogels include those containing collagen, hyaluronic acid-based hydrogels, and decellularized natural ECM from mammalian tissues.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Electrical Stimulation of Cardiac Cells to Produce Secretome

Although much attention has been devoted to the role of chemical and architectural cues in cell behavior, endogenous electrical signals (electrical cues) existing in both normal and injured tissue are less studied. These electrical signals are originally mediated by endogenous ion flows, electric fields, and voltage gradients that ultimately derive from the action of ion channels and pumps. Application of such external electrical fields recently has been considered as a tool to induce tissue regeneration and progressive development of conductive and contractile properties of heart tissue. Studies show electrical stimulation increase the expression of cardiac-specific genes and the increase of differentiation, promote ventricular-like phenotypes, and improved the calcium handling of cardiomyocytes. However, delivering electrical stimulation to the diseased tissue, in a minimally invasive way, remains a challenge.

It was hypothesized that trophic paracrine factors (i.e., the cell secretome), released as a result of electrical stimulation of cardiomyocytes, could be effective for use in heart tissue repair. This examples is directed to development of an injectable secretome-hydrogel system for repairing heart tissue, in which the secretome derives from electrically stimulated cells.

FIG. 1 is a schematic showing electrical stimulation used to produce a secretome for tissue engineering and regenerative medicine application.

Figure 2:
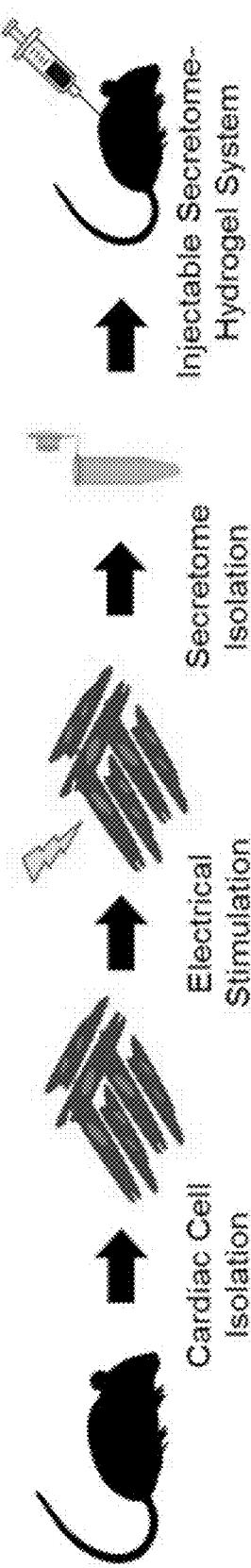
FIG. 2 a schematic of experiments. Cardiac cells are isolated from mouse heart and electrically stimulated. Secretome of the cells is collected, characterized, combined with a hydrogel and injected in the MI mouse model.

FIG. 2 a schematic of experiments. Cardiac cells are isolated from mouse heart and electrically stimulated. Secretome of the cells is collected, characterized, combined with a hydrogel and injected in the MI mouse model.

Figure 3:
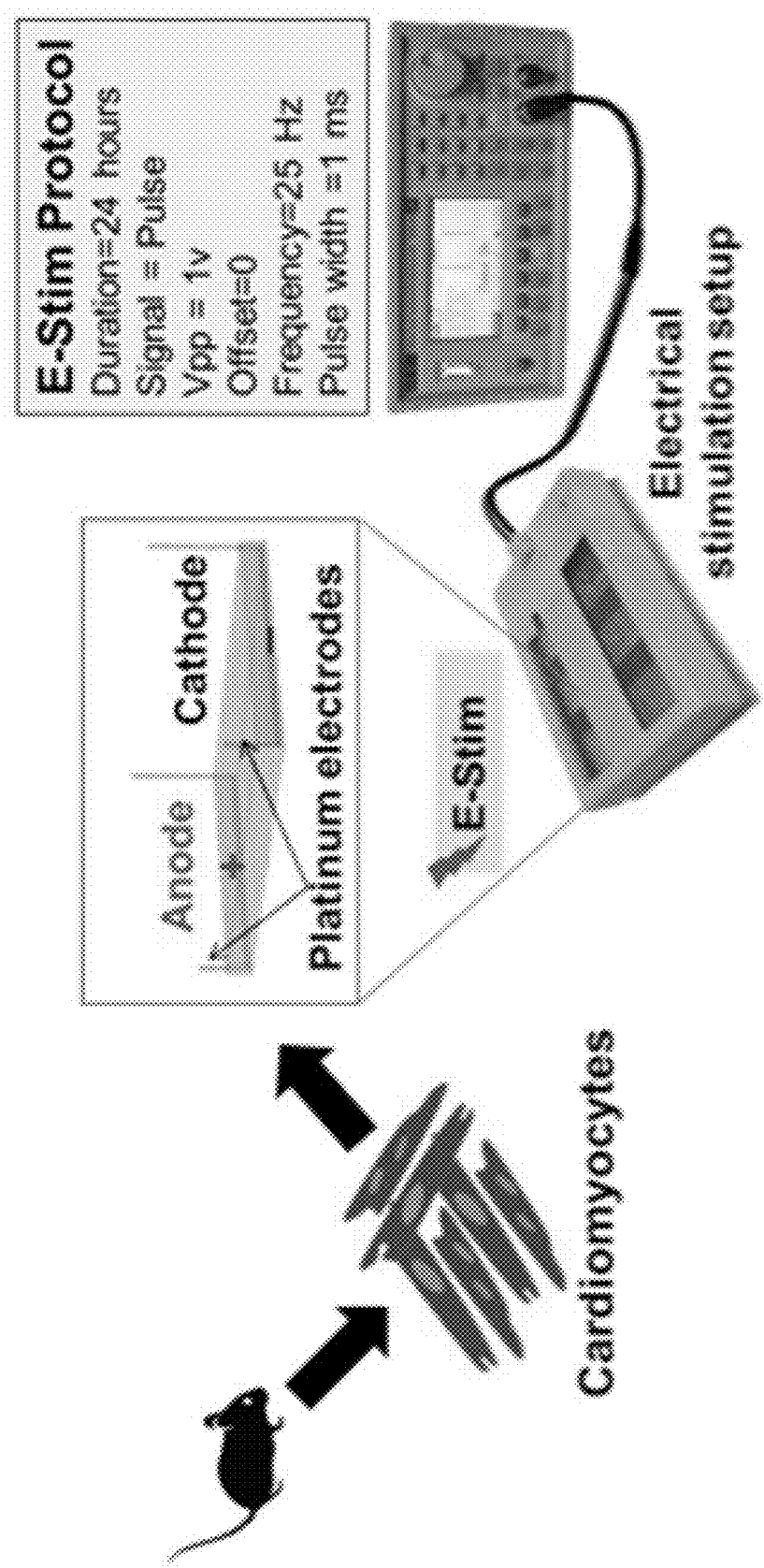
FIG. 3 a schematic of electrical stimulation setup. Cardiomyocytes were isolated from the mouse heart and cultured at least for 2 hours. Electrical stimulation setup applied E-Stim protocol for 24 hours on the cells.

FIG. 3 a schematic of electrical stimulation setup. Cardiomyocytes were isolated from the mouse heart and cultured at least for 2 hours. Electrical stimulation setup applied E-Stim protocol for 24 hours on the cells.

Figure 4B:
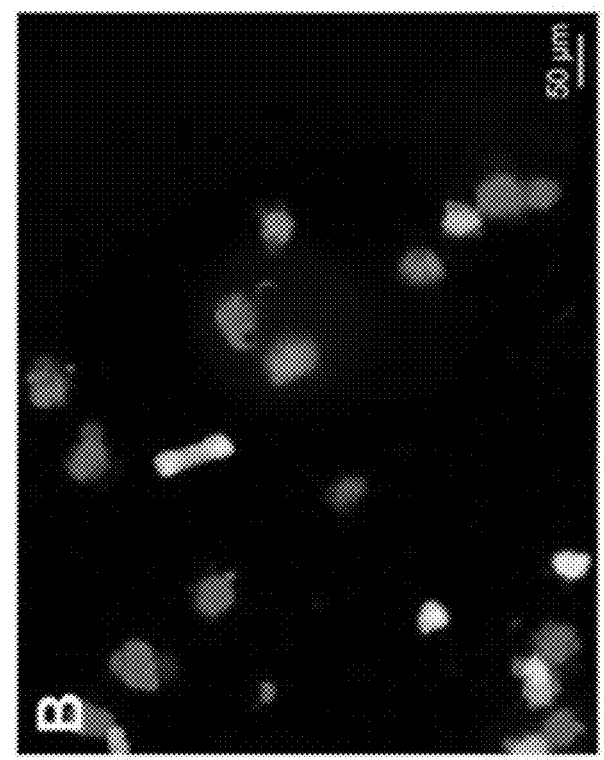
FIGS. 4A and 4B show live/dead staining of cardiomyocytes after electrical stimulation for 24 hours (FIG. 4A) and no electrical stimulation (FIG. 4B).
Figure 4A:
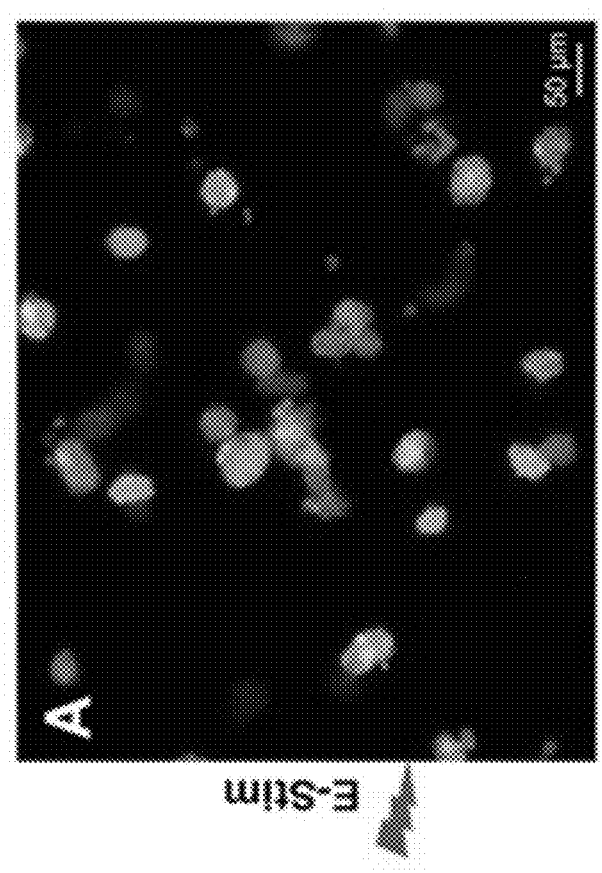
Figure 4D:
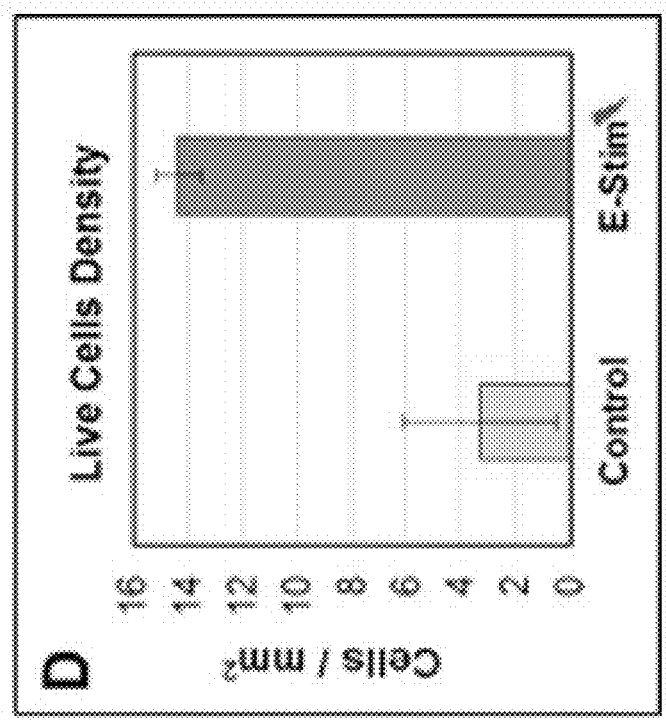
FIG. 4D is a bar graph showing live cell density (cells/mm$^2$) in electrical stimulation and control (n=6).
Figure 4C:
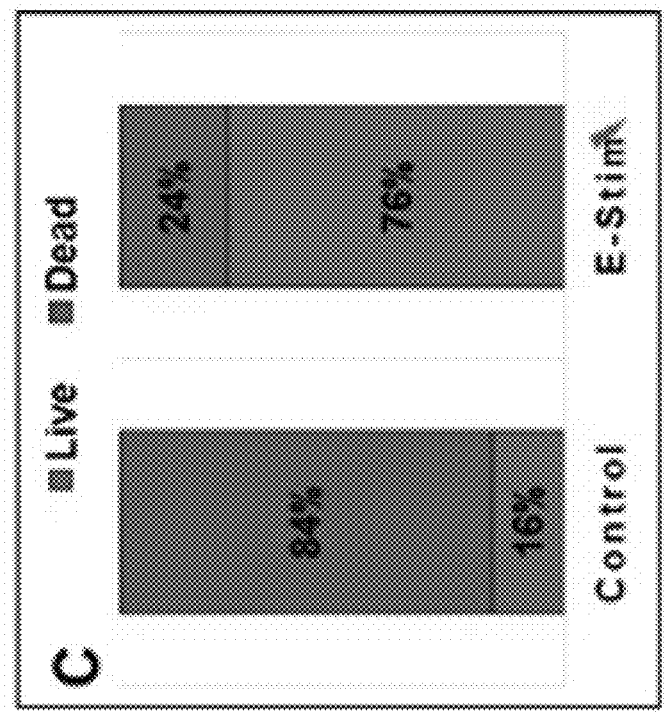
FIG. 4C is a bar graph showing semi-quantified data from 5× images of live/dead staining (n=3), p<0.005.

FIGS. 4A and 4B show live/dead staining of cardiomyocytes after electrical stimulation for 24 hours (FIG. 4A) and no electrical stimulation (FIG. 4B). FIG. 4C is a bar graph showing semi-quantified data from 5× images of live/dead staining (n=3), p<0.005. FIG. 4D is a bar graph showing live cell density (cells/mm$^2$) in electrical stimulation and control (n=6).

Figure 5:
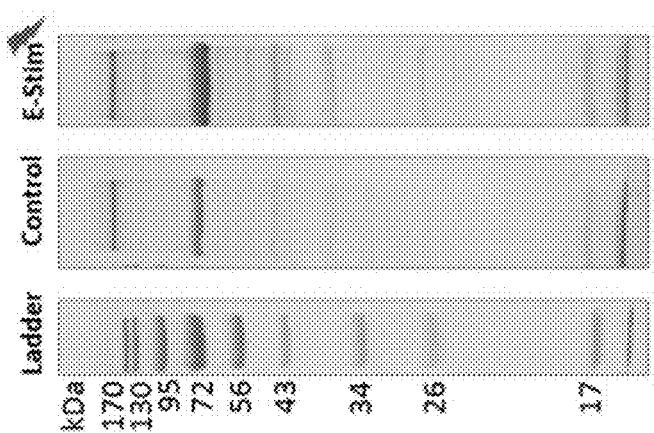
FIG. 5 shows total protein content. SDS-PAGE was run on secretome samples of electrically stimulated cells and control. The same amount of protein was loaded in each well. E-stim secretome shows darker bands.

FIG. 5 shows total protein content. SDS-PAGE was run on secretome samples of electrically stimulated cells and control. The same amount of protein was loaded in each well. E-stim secretome shows darker bands.

Figure 6:
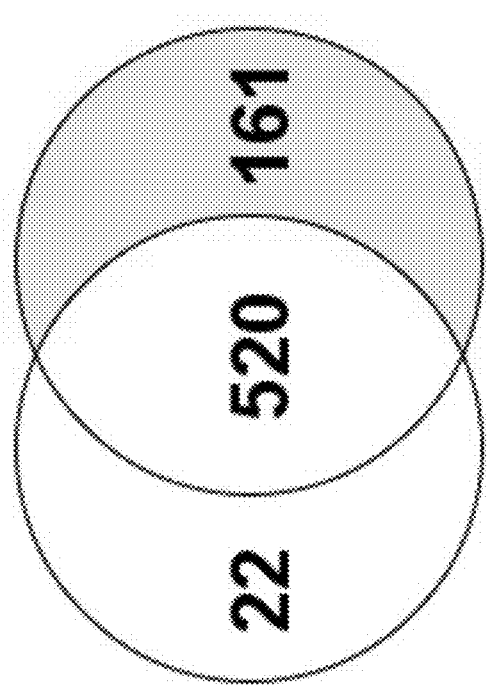
FIG. 6 shows from mass spec analysis that the secretome from stimulated cells contains 161 unique proteins, while the control has only 22 unique proteins.

FIG. 6 shows from mass spec analysis that the secretome from stimulated cells contains 161 unique proteins, while the control has only 22 unique proteins.

Figure 7:
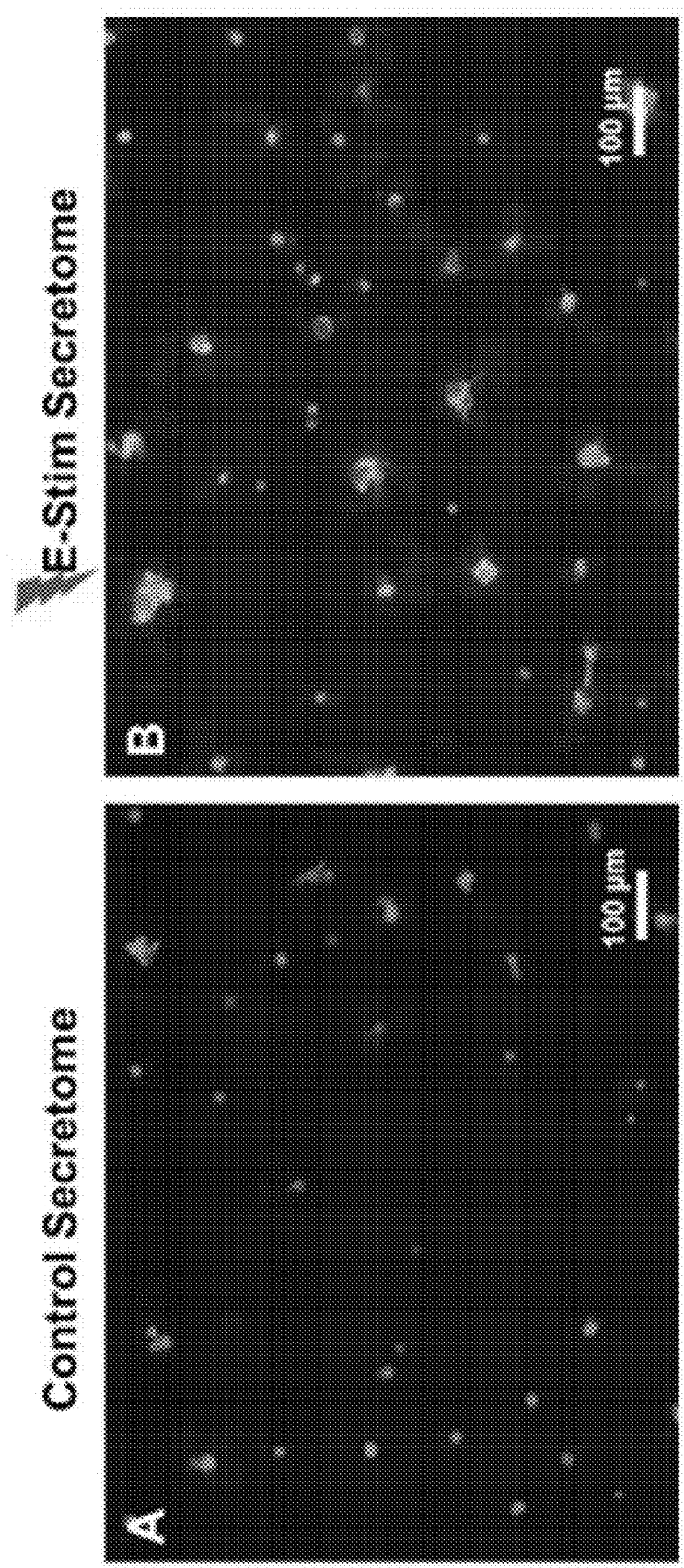
FIGS. 7A and 7B show results of angiogenesis assay. HUVECs were cultured on Matrigel scaffolds and treated with secretome from cardiomyocytes control (non-stimulated) secretome (FIG. 7A) and electrical stimulation secretome (FIG. 7B). HUVECs spread more when treated with secretome from electrically stimulated cells versus control.

FIGS. 7A and 7B show results of angiogenesis assay. HUVECs were cultured on Matrigel scaffolds and treated with secretome from cardiomyocytes control (non-stimulated) secretome (FIG. 7A) and electrical stimulation secretome (FIG. 7B). HUVECs spread more when treated with secretome from electrically stimulated cells versus control.

Example 2: Electrical Stimulation of Schwann Cells

Local electrical stimulation (E-stim) of the damaged tissue after spinal cord injury (SCI) promotes neural regeneration. However, delivering E-stim to the tissue, in a minimally invasive way, remains a challenge and the direct mechanism by which electrical stimulation induces regeneration is unclear. A tissue engineering approach, which mimics the physical and chemical microenvironment of the extracellular matrix and administers neurotrophic and neurotropic factors, derived from electrically stimulated cells, is an innovative strategy that can overcome these challenges.

This Example is directed to the development of regeneration cues for SCI repair via an injectable scaffold derived from decellularized nerve tissue in combination with novel secretome-based therapeutic elements from electrically stimulated cells.

Figure 8:
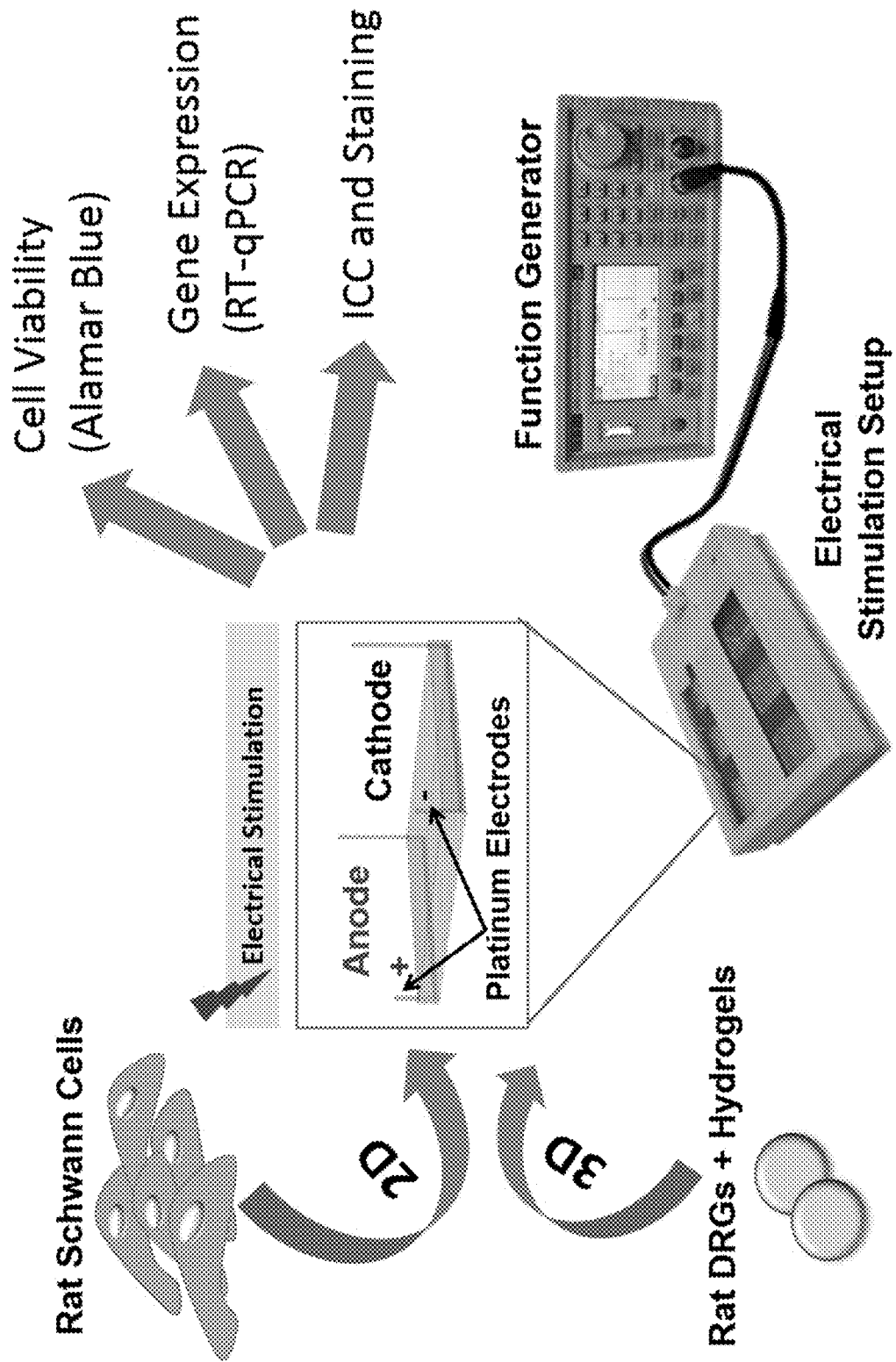
FIG. 8 is a schematic of an experimental design.

FIG. 8 is a schematic of an experimental design.

TABLE 1

Electrical stimulation regimes

| Regime | Shape | Vamp (mV) | Voffset (mV) | Frequency (Hz) | Vmax (mv) | E-field (mV/mm) |
|---|---|---|---|---|---|---|
| R1 | sine | 150 | 75 | 200 | 144.5 | 4.3 |
| R2 | sine | 220 | 110 | 20 | 154.8 | 4.6 |
| R3 | sine | 350 | 175 | 200 | 337.1 | 10.1 |
| R4 | sine | 500 | 250 | 20 | 351.9 | 10.5 |
| R5 | sine | 700 | 350 | 200 | 674.2 | 20.1 |
| R6 | sine | 1000 | 500 | 20 | 703.8 | 21.0 |
| R7 | sine | 2000 | 1000 | 20 | 1407.7 | 42.0 |
| R8 | square | 700 | 350 | 1 | 6.3 | 0.2 |
| R9 | pulse | 1000 | 500 | 20 | 0.6 | 1.8E–02 |
| R10 | pulse | 1000 | 500 | 50 | 0.6 | 1.8E–02 |

Figure 9:
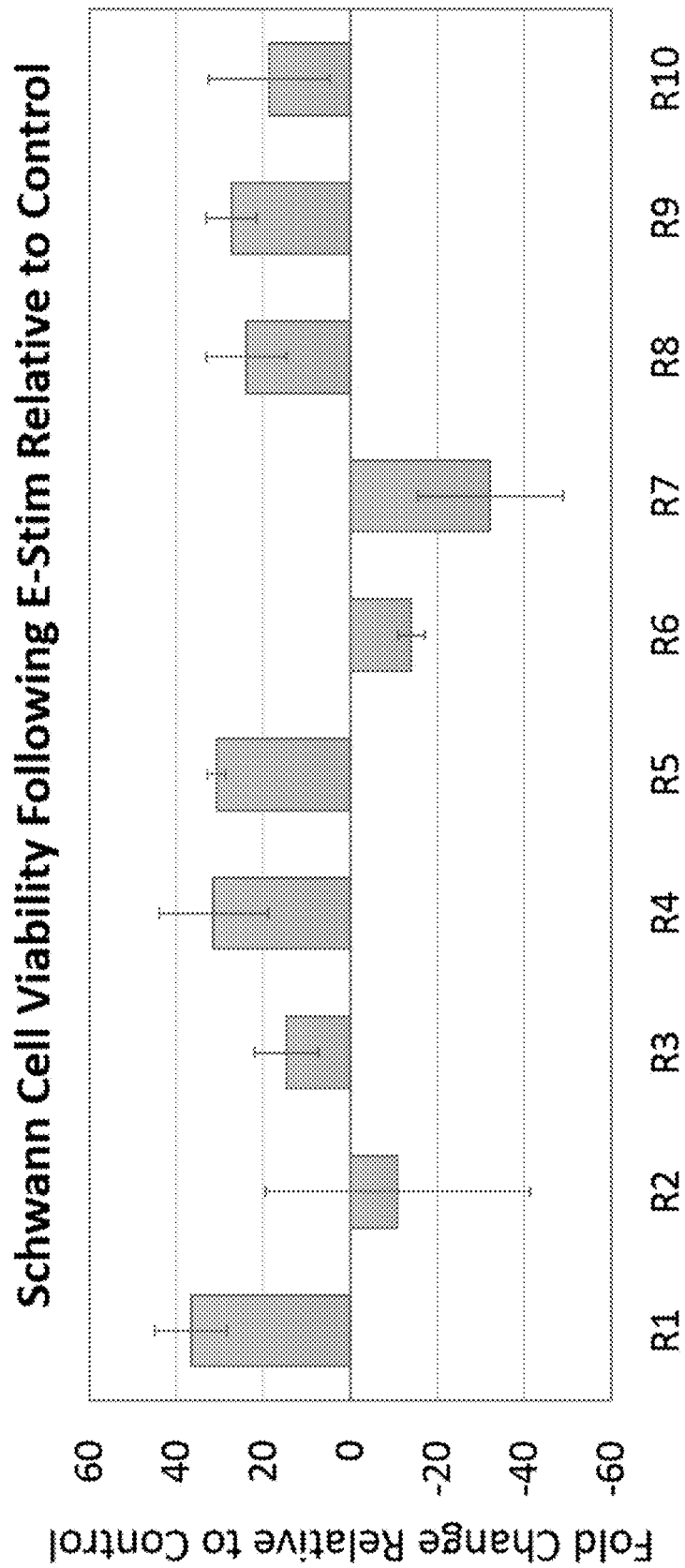
FIG. 9 is a bar graph showing cell viability after 3 days of E-Stim. R4, R6 and R7 experiments replicated 3 times. All other experiments run once-in all experiments (n=3).

FIG. 9 is a bar graph showing cell viability after 3 days of E-Stim. R4, R6 and R7 experiments replicated 3 times. All other experiments run once-in all experiments (n=3).

Figure 10B:
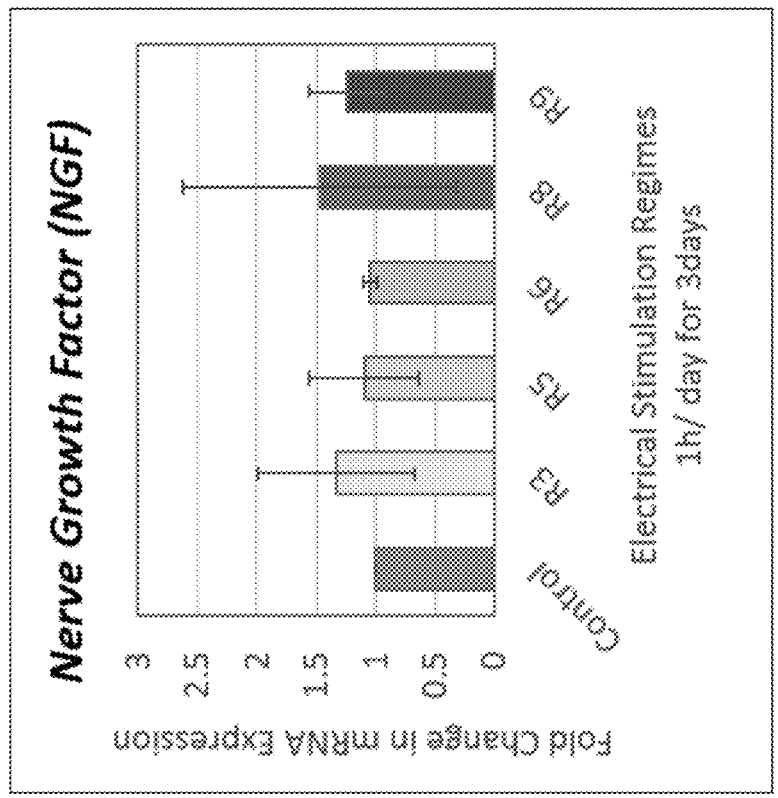
FIGS. 10A and 10B are bar graphs showing fold change in mRNA expression of myelin basic protein (MBP) (FIG. 10A) and nerve growth factor (NGF) (FIG. 10B) after electrical stimulation 1 h/day for 3 days. Stimulation regimes are shown in Table 1.
Figure 10A:
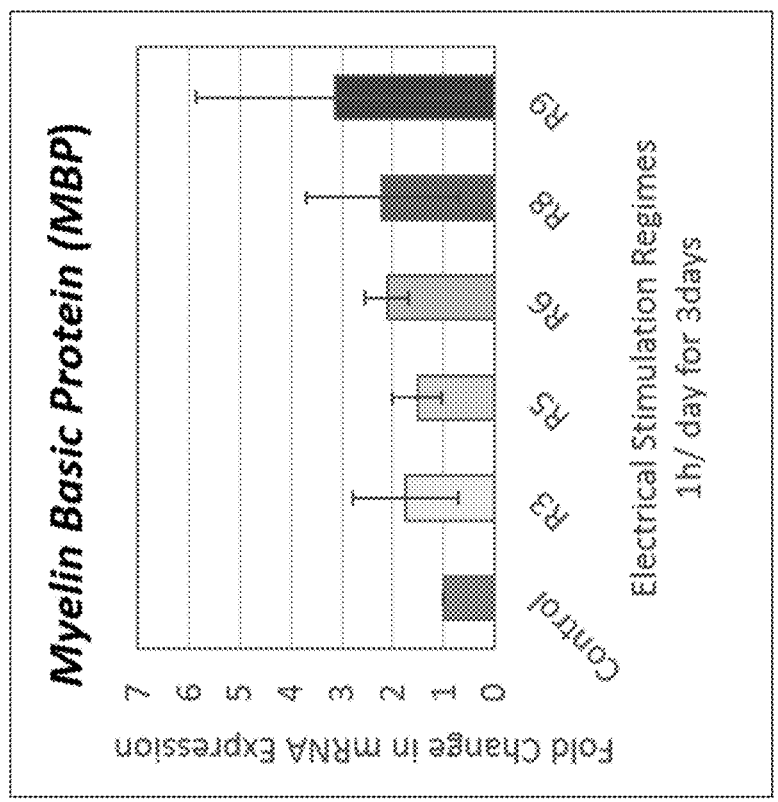

FIGS. 10A and 10B are bar graphs showing fold change in mRNA expression of myelin basic protein (MBP) (FIG. 10A) and nerve growth factor (NGF) (FIG. 10B) after electrical stimulation 1 h/day for 3 days. Stimulation regimes are shown in Table 1.

TABLE 2

Result summary

| Regime | Shape | Vamp (mV) | Frequency (Hz) | E-field (mV/mm) | Viability | MBP | NGF |
|---|---|---|---|---|---|---|---|
| R1 | sine | 150 | 200 | 4.3 | ↑++ | | |
| R2 | sine | 220 | 20 | 4.6 | ↓– | | |
| R3 | sine | 350 | 200 | 10.1 | ↑+ | + | + |
| R4 | sine | 500 | 20 | 10.5 | ↑++ | | |
| R5 | sine | 700 | 200 | 20.1 | ↑++ | + | 0 |
| R6 | sine | 1000 | 20 | 21.0 | ↓– | ++ | 0 |
| R7 | sine | 2000 | 20 | 42.0 | ↓–– | | |
| R8 | square | 700 | 1 | 0.2 | ↑+ | ++ | + |
| R9 | pulse | 1000 | 20 | 1.8E–02 | ↑++ | +++ | + |
| R10 | pulse | 1000 | 50 | 1.8E–02 | ↑+ | | |

Figures 11A, 11B:
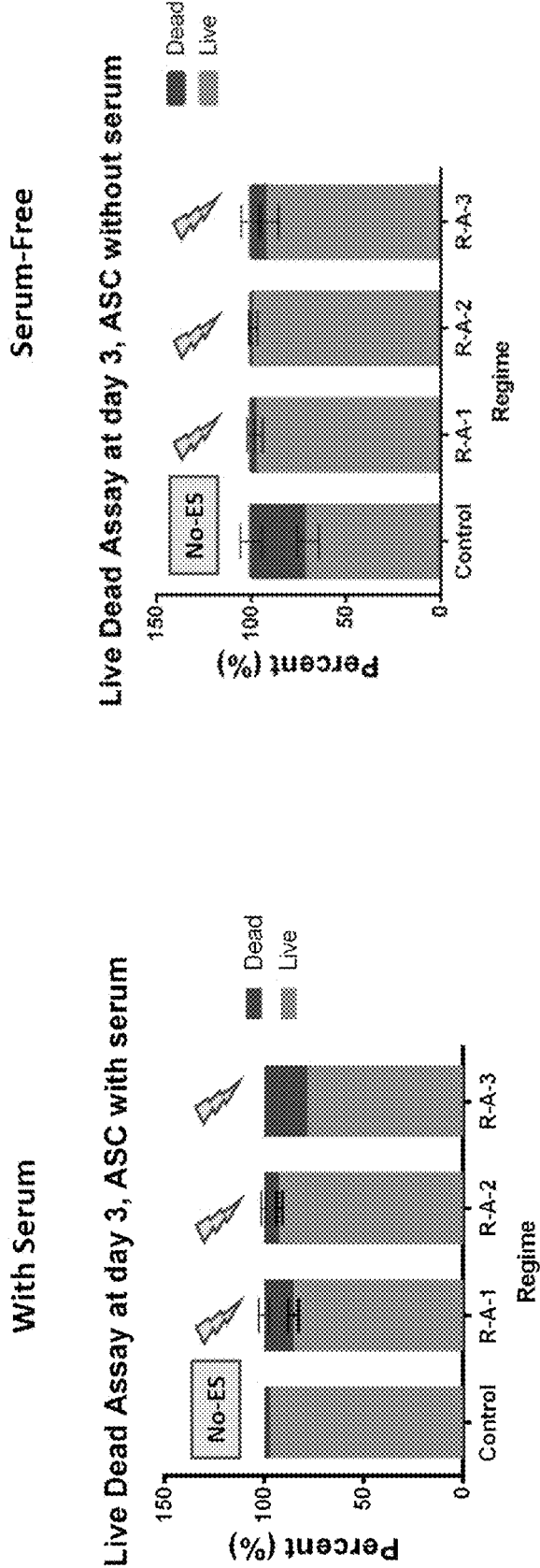
FIGS. 11A and 11B are bar graph showing results of live/dead assays (%) at day three, ASC with (FIG. 11A) and without (FIG. 11B) serum after electrical stimulation. Stimulation regimes are shown in Table 3.

Example 3: Development and Characterization of the Secretome from Electrically Stimulated Adipose-Derived Stromal/Stem Cells (ASC) for Tissue Engineering FIGS. 11A and 11B are bar graph showing results of live/dead assays (%) at day three, ASC with (FIG. 11A) and without (FIG. 11B) serum after electrical stimulation. Stimulation regimes are shown in Table 3.

TABLE 3

| Regime | Shape | $V_{amp}$ (mV) | Offset | Frequency (Hz) | $V_{max}$ (mV) | Electrical Field (mV/mm) | Pulse Width (ms) |
|---|---|---|---|---|---|---|---|
| R-A-1 | Pulse | 674 | 0 | 1 | 674 | 20.12 | 0.5 |
| R-A-2 | Pulse | 674 | 0 | 1000 | 674 | 20.12 | 0.5 |
| R-A-3 | Pulse | 674 | 0 | 20 | 674 | 20.12 | 0.5 |

Figures 12A, 12B:
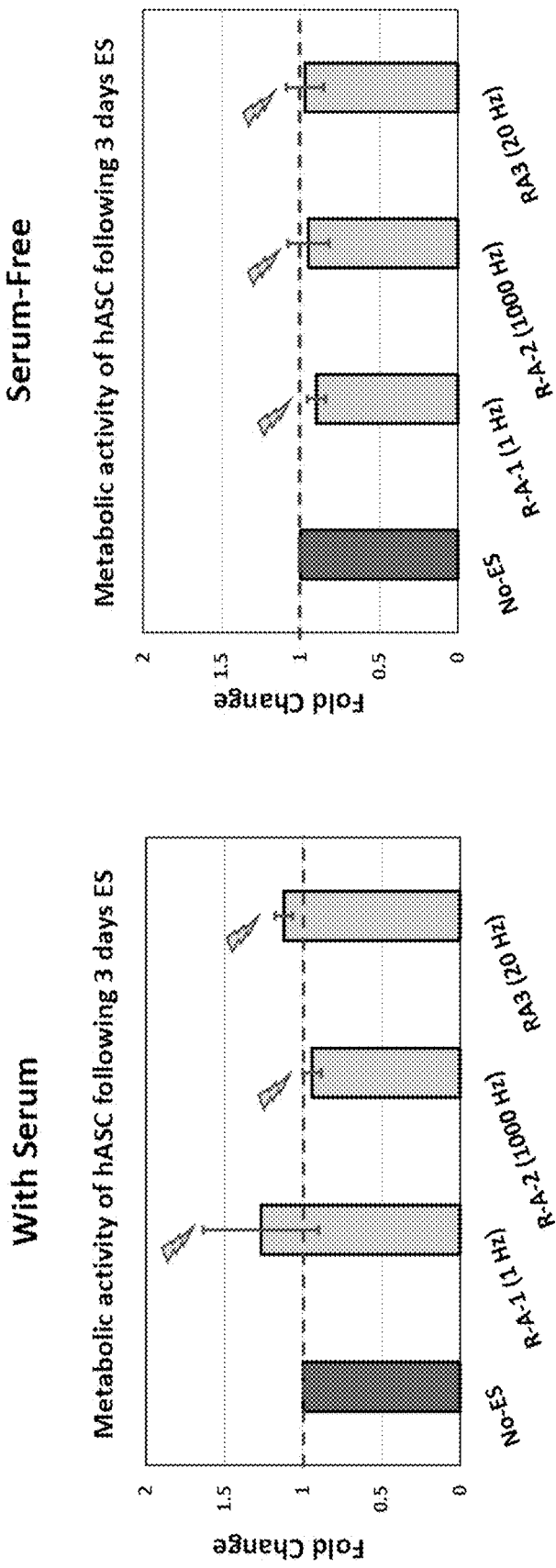
FIGS. 12A and 12B are bar graph showing fold change at day three, ES with (FIG. 12A) and without (FIG. 12B) serum after electrical stimulation.

FIGS. 12A and 12B are bar graph showing fold change at day three, ES with (FIG. 12A) and without (FIG. 12B) serum after electrical stimulation.

Figure 13A:
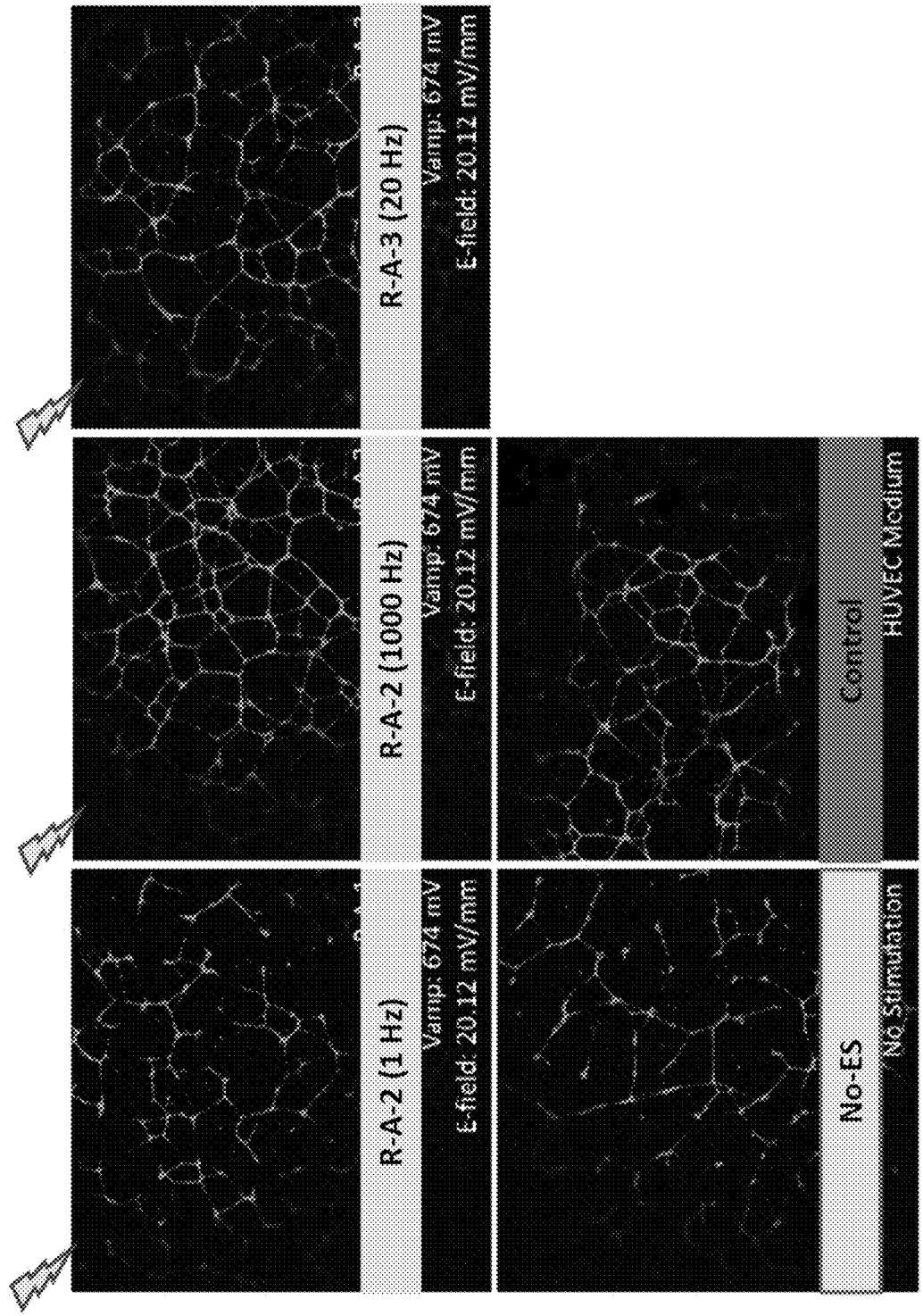
FIGS. 13A to 13E are images (FIG. 13A) and bar graphs (FIGS. 13B to 13E) showing results of HUVEC tube formation in vitro assays in response to serum-free secretome.
Figure 13C:
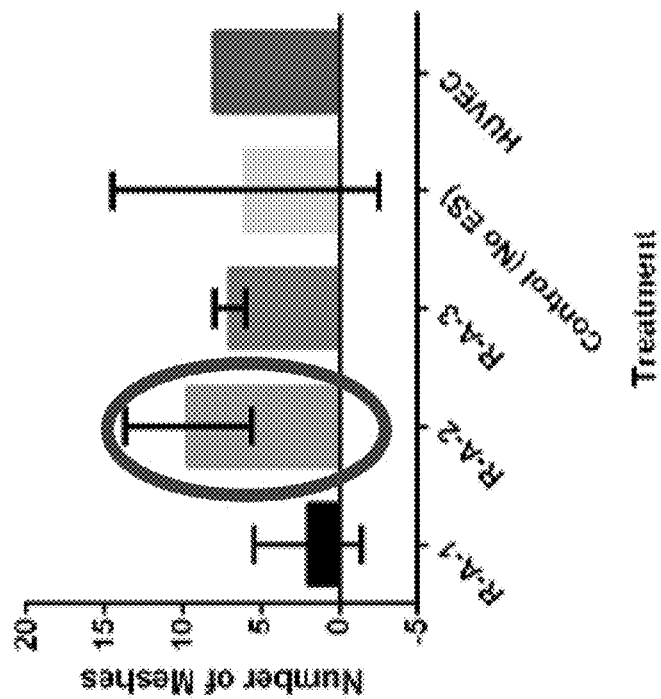
Figure 13B:
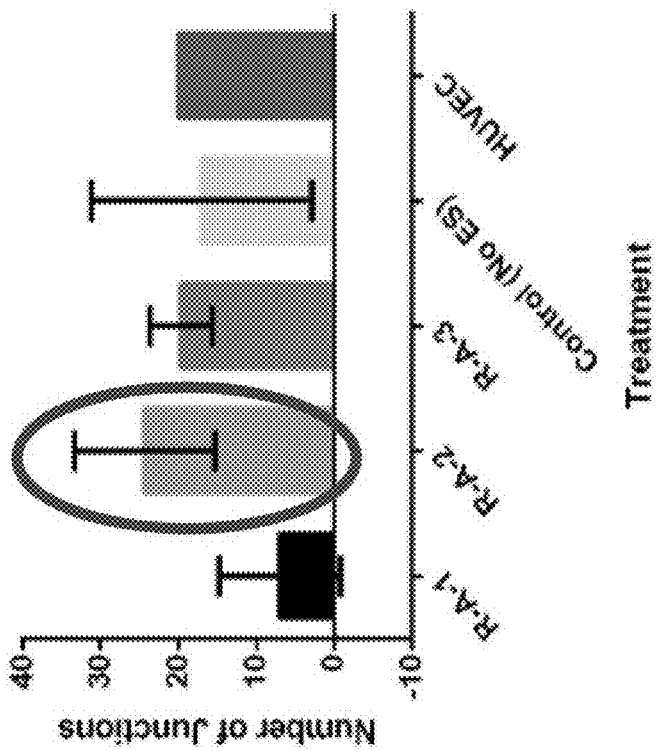
Figure 13E:
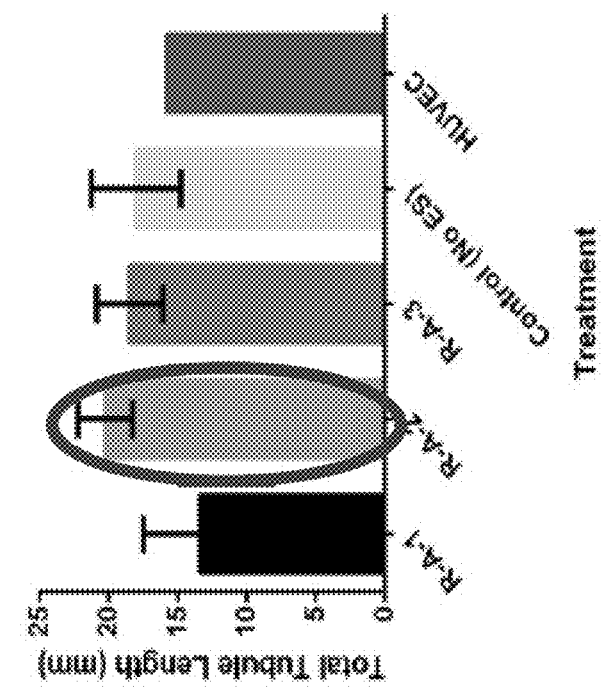
Figure 13D:
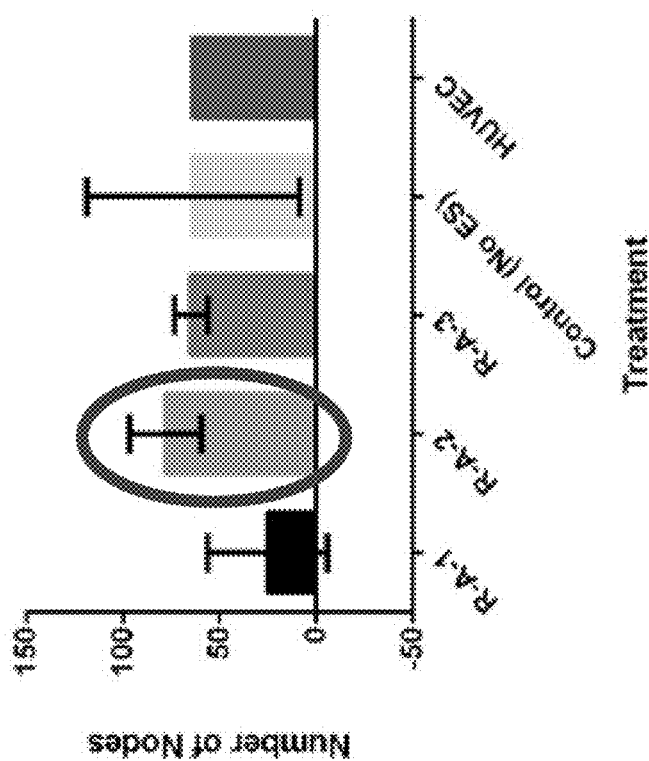

FIGS. 13A to 13E are images (FIG. 13A) and bar graphs (FIGS. 13B to 13E) showing results of HUVEC tube formation in vitro assays in response to serum-free secretome. FIGS. 13B to 13E show effect of secretome on number of junctions (FIG. 13B), number of meshes (FIG. 13C), number of nodes (FIG. 13D), and total tubule length (FIG. 13E).

Figure 14B:
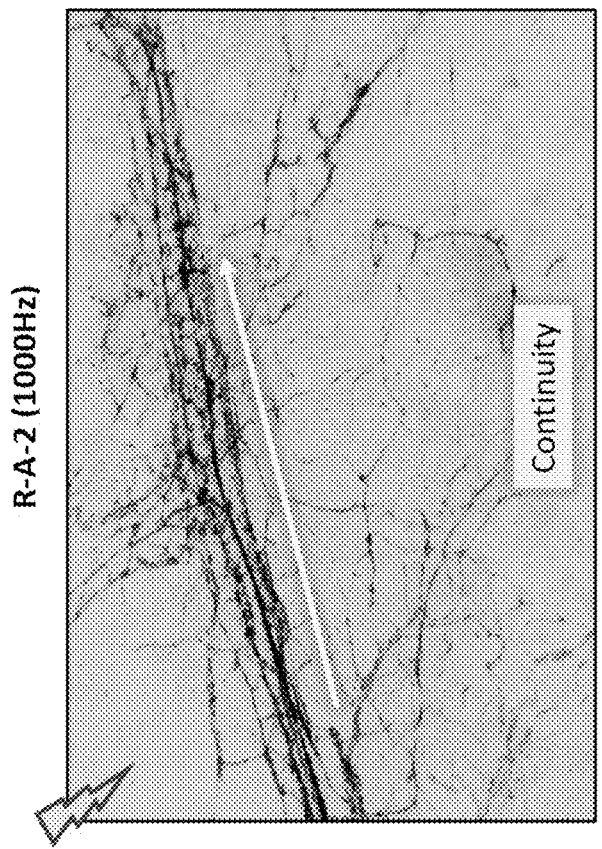
FIGS. 14A and 14B are images showing results of mesentery ex vivo model in response to serum-free secretome without ES (FIG. 14A) or with 1000 Hz ES (FIG. 14B).
Figure 14A:
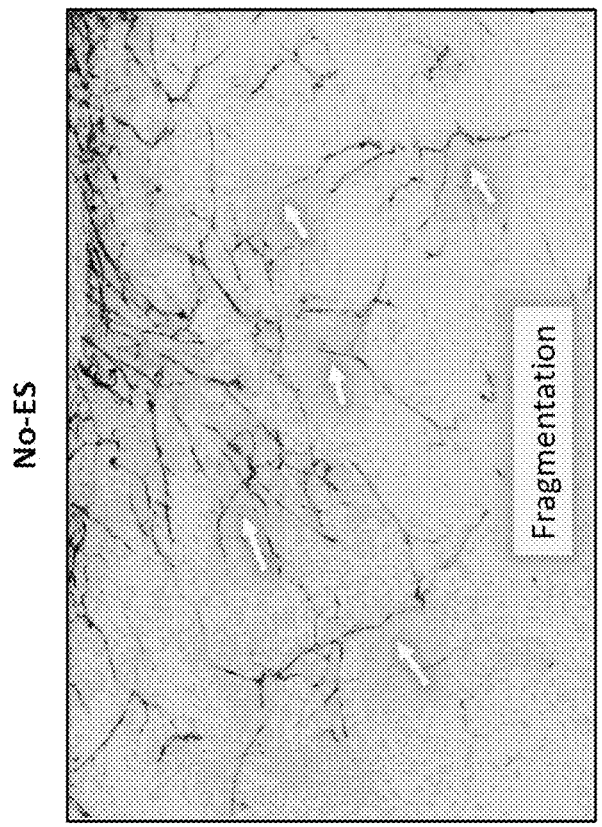

FIGS. 14A and 14B are images showing results of mesentery ex vivo model in response to serum-free secretome without ES (FIG. 14A) or with 1000 Hz ES (FIG. 14B).

Figure 15A:
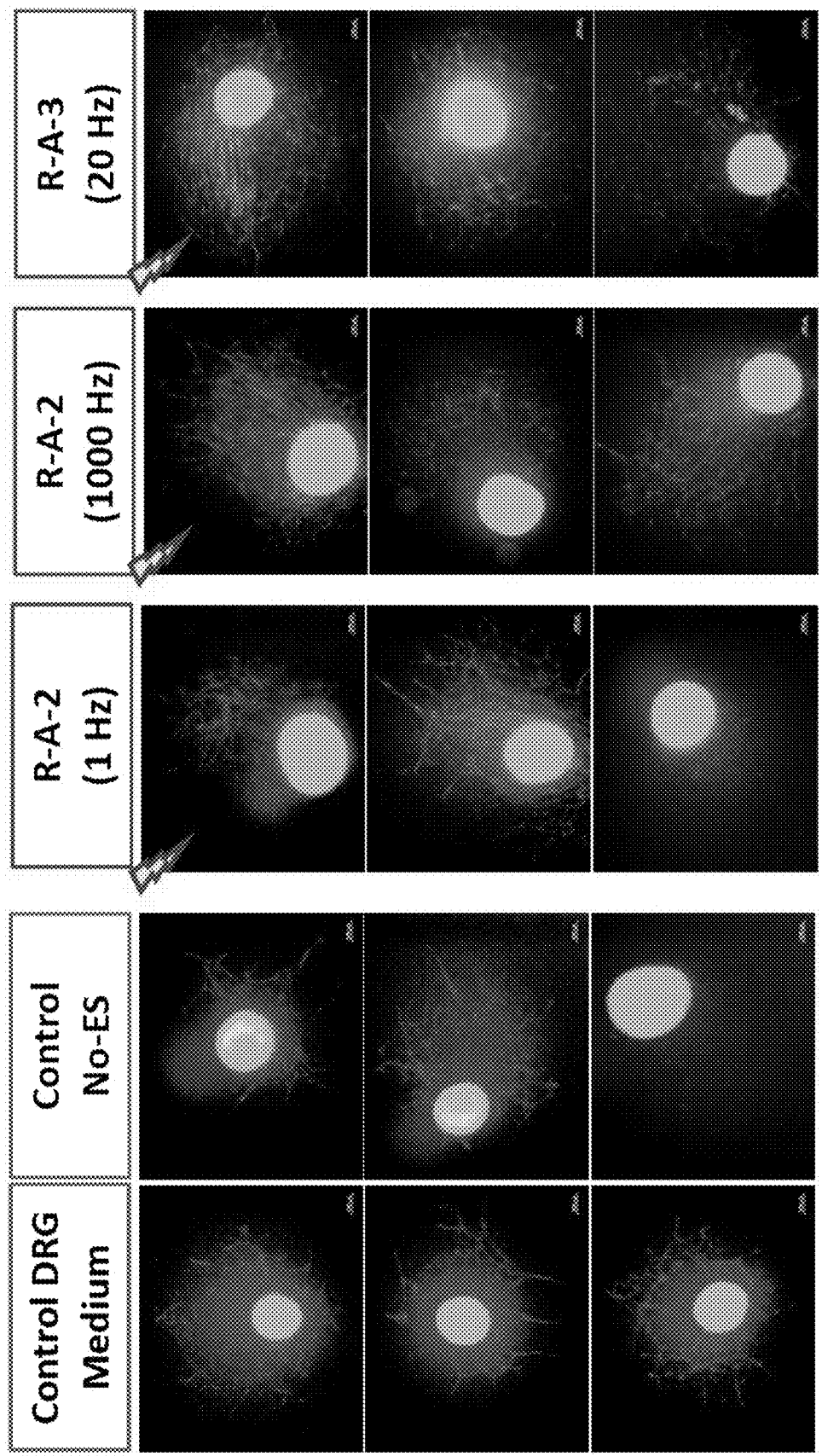
FIGS. 15A to 15C are images (FIG. 15A) and bar graphs (FIGS. 15B and 15C) showing neurite out growth (DRG culture) in response to serum-free secretome.
Figure 15C:
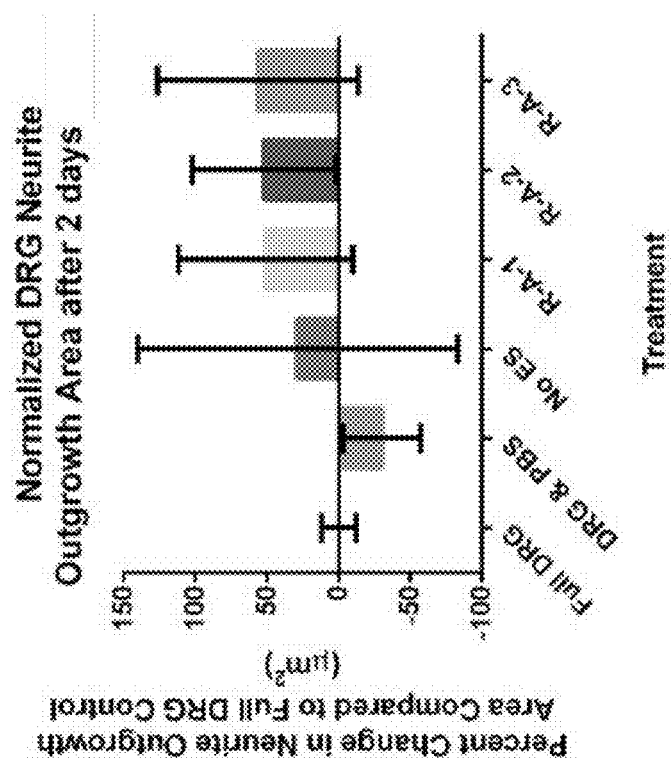
Figure 15B:
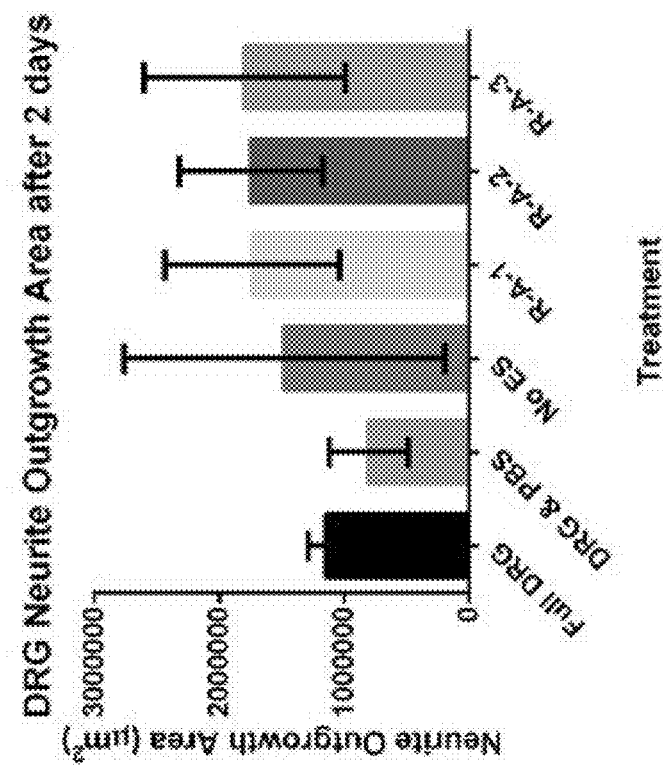

FIGS. 15A to 15C are images (FIG. 15A) and bar graphs (FIGS. 15B and 15C) showing neurite out growth (DRG culture) in response to serum-free secretome. FIGS. 15B and 15C show DRG neurite outgrowth area after 2 days (FIG. 15B) and normalized DRG neurite outgrowth area after 2 days (FIG. 15C).

Figure 16:
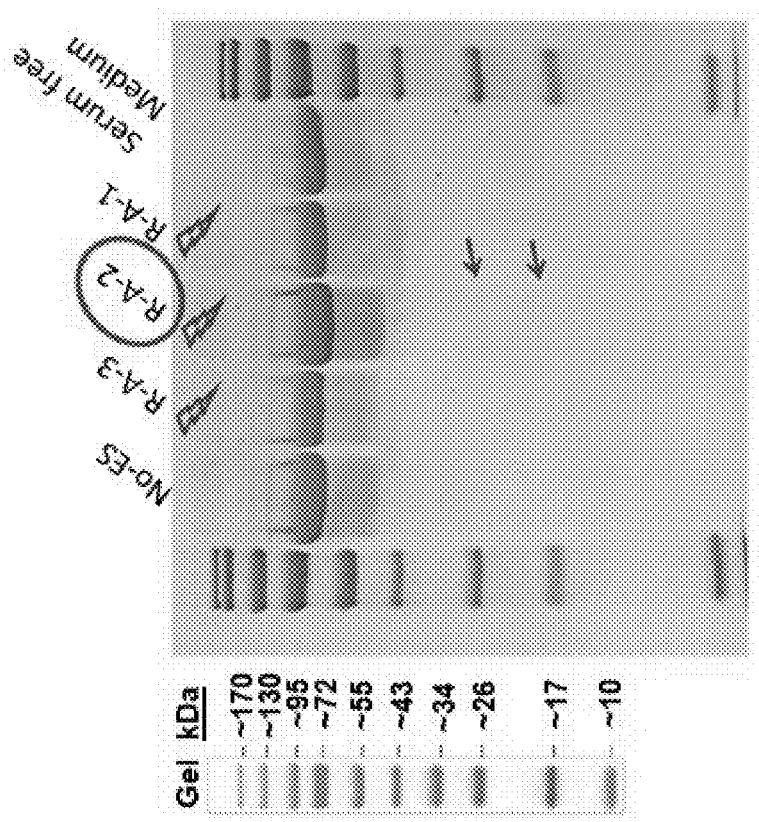
FIG. 16 is an image of a gel showing secretome SDS page results. 10 μg of protein (entire sample) was loaded into each well and run on 12.5% Tris-HCL criterion precast gel. Arrows indicate slight band.
Figure 17A:
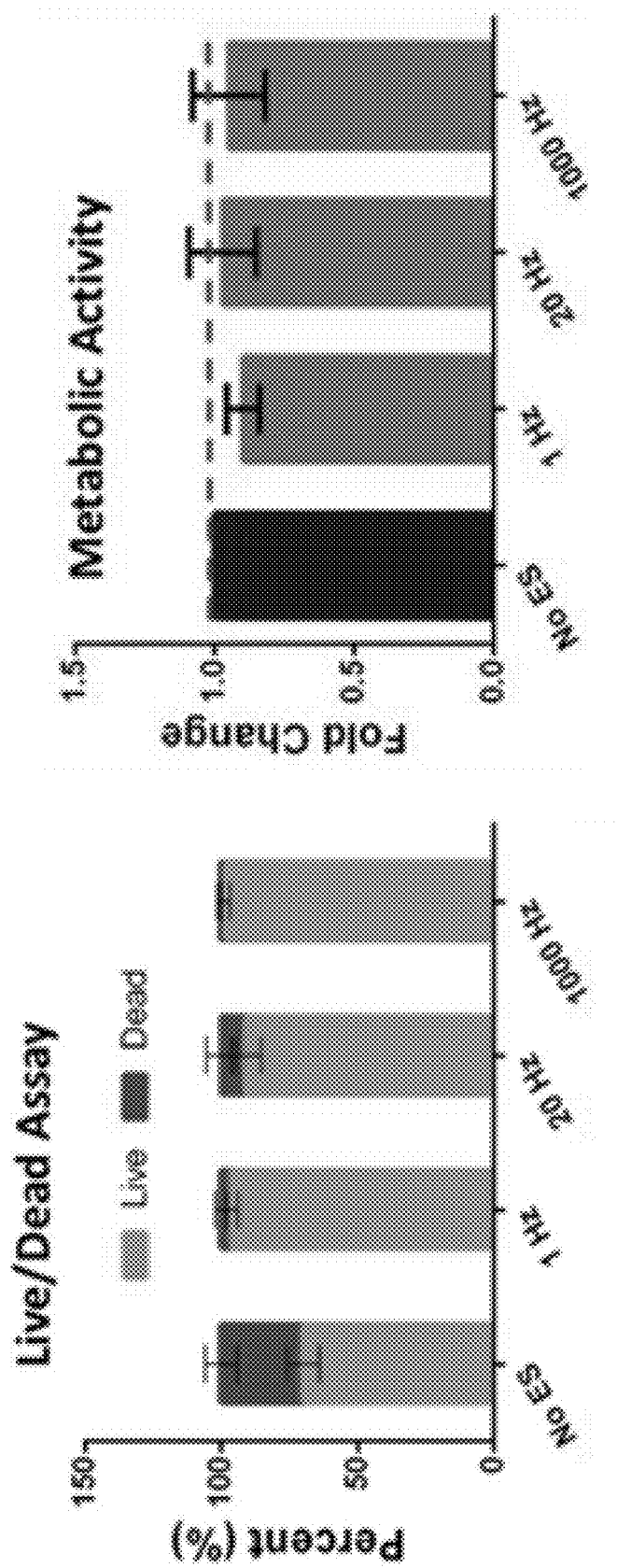
FIG. 17A contains bar graphs showing viability and metabolic activity of the cells after 3 days ES normalized to the control.
Figure 17B:
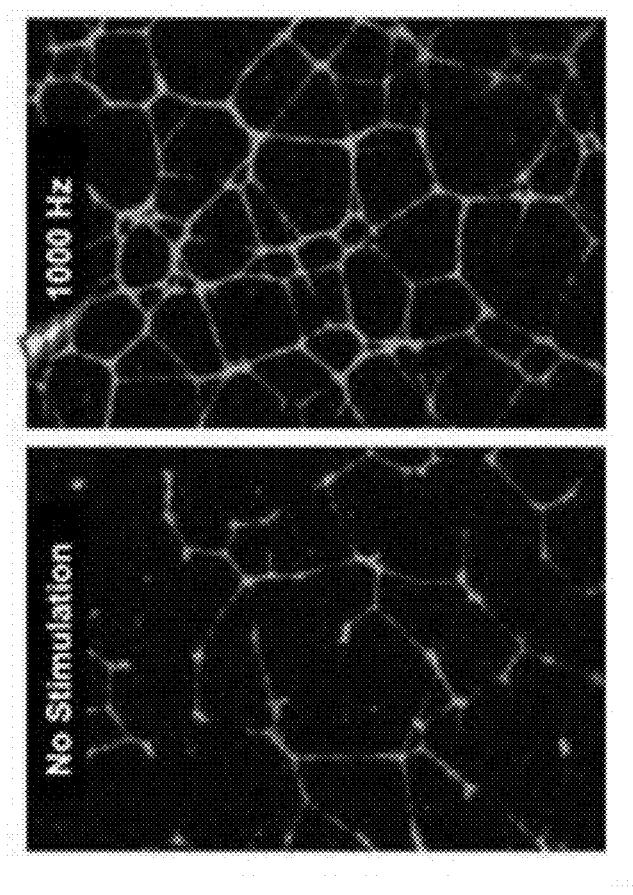
FIGS. 17B and 17C are bar graphs and an images showing HUVECs tube formation (FIG. 17B) and neurite out growth from DRG explants (FIG. 17C), after treatment with secretome from electrically stimulated hASCs.
Figure 17B:
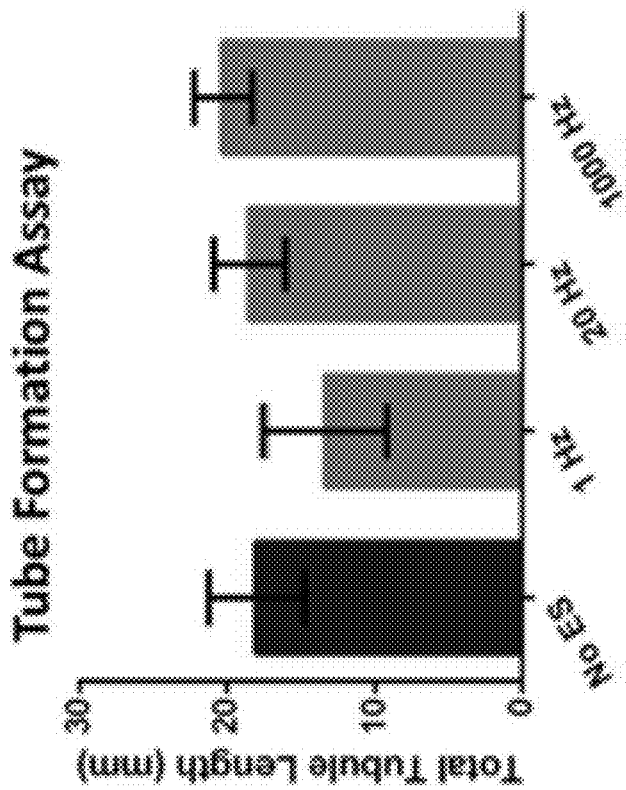
Figure 17C:
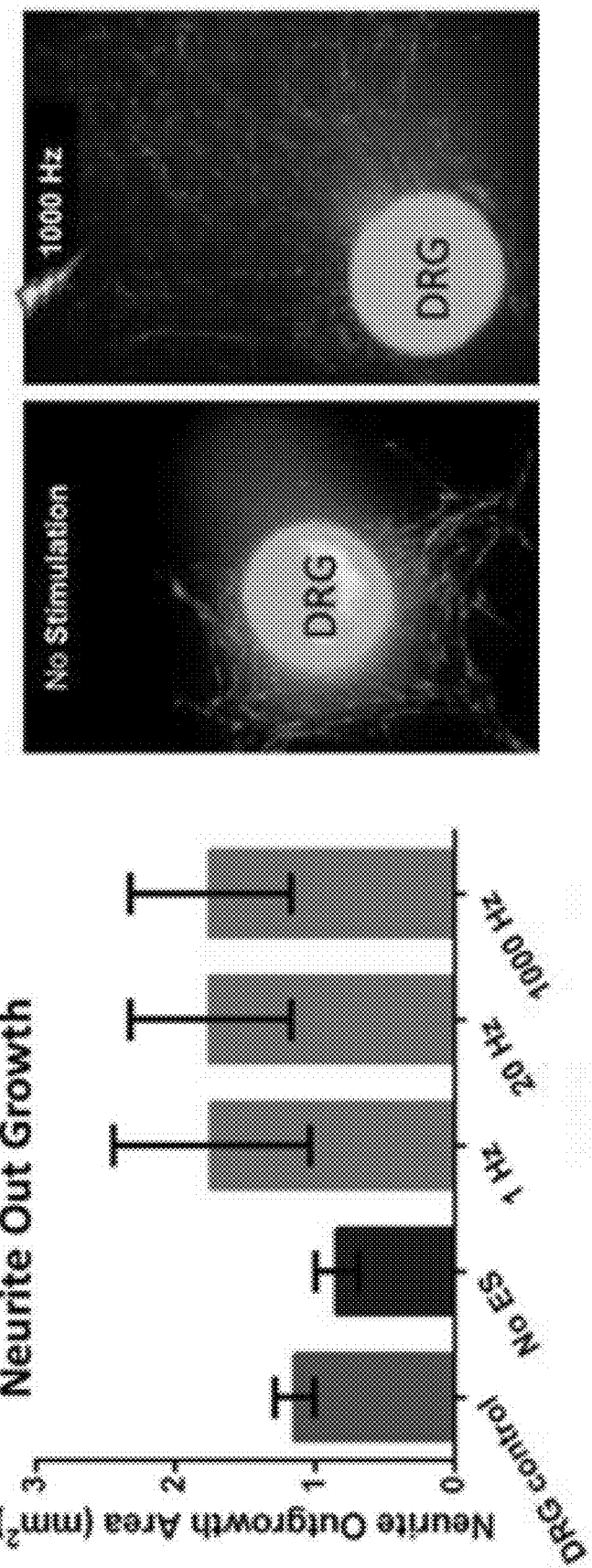

FIG. 16 is an image of a gel showing secretome SDS page results. 10 μg of protein (entire sample) was loaded into each well and run on 12.5% Tris-HCL criterion precast gel. Arrows indicate slight band.

Summary

H-ASCs viability do not change significantly by 20 mV/mm ES in different frequencies. H-ASCs metabolic activity do not change significantly by 20 mV/mm ES in different frequencies. H-ASCs secretome from 1000 Hz ES significantly improves angiogenesis (continuity and network structure). H-ASCs secretome from 1000 Hz ES improves neurite out growth (*need to revisit data for better SD). H-ASCs secretome from 1000 Hz ES contains extra protein bands (** in the pipe-line).

Example 4: Secretome from Electrically Stimulated Mesenchymal Stromal/Stem Cells Increases Neurite Outgrowth and Angiogenesis In Vitro Materials and Methods hASCs were obtained from Lonza and cultured at a density of $1 \times 10^5$ cells/well in an electrobioreactor, which previously was developed by Mobini et al. (Wei X, et al. Stem Cells, 2009 27(2):478-88). One day after seeding, culture medium was replaced with serum-free (StemPro®) medium, and cells were electrically stimulated with either 1 Hz, 20 Hz, or 1000 Hz pulses, with intensity of 20 mV/mm, 1 hour/day for 3 days (n=6). At day 4, the conditioned media were collected and dead cells and debris removed with centrifugation at 300×g and stored in −80° C. Cell metabolic activity and viability were quantified via alamarBlue and Live/Dead assays, respectively. Neonatal rat dorsal root ganglia (DRG) explants and human umbilical vein endothelial cells (HUVECs) were treated with secretome from electrically stimulated hASCs and controls (non-stimulated) to assess neurite outgrowth and tube formation of endothelial cells, respectively. Blinded analysis was performed on the images and quantified using ImageJ.

Results and Discussion

Results showed more live hASCs are detectable in the electrically stimulated groups than the non-stimulated control after 3 days, though the metabolic activity did not change. We found more interconnected tube-like structure in the group treated with secretome from hASCs stimulated by 1000 Hz pulses in comparison to no-ES group. Greater length of neurite outgrowth was detected in DRG explants exposed to the secretome from ES hASCs comparing to no-ES and secretome-free controls.

CONCLUSIONS

In summary, secretome isolated from hASCs exposed to 20 mV/mm and 1 kHz electrical pulses revealed remarkable improvement in neurite outgrowth in DRGs and interconnected tube-like structure in HUVECs. This result demonstrates the pro-regenerative effect of electrically enhanced secretome from hASCs, which can be utilized as injectable therapeutics for SCI management.

Example 5: Electrical Stimulation of ASCs

A direct current bioreactor with parallel platinum electrodes was used to provide an electrical field of 20 mV/mm, with a square pulse (500 μs), at a frequency of 1 Hz, 20 Hz, or 1000 Hz, for a duration of 1 hour per day for 3 days. Cell lysates were collected 24 hours after day 3 of stimulation.

Lonza adipose-derived stem cells (ASCs, cat #: PT-5006) were cultured in a growth media containing DMEM/F12 with 10% FBS, 1% Pen/Strep; and in a stimulation media containing Stempro (Gibco, no serum component).

Gene expression analysis was conducted using polymerase chain reaction (PCR). mRNA was obtained from ASC lysates and converted to cDNA for real-time PCR to measure vascular endothelial growth factor A (VEGFA), tissue inhibitor of metalloproteinase 1 (TIMP1), or brain derived neurotrophic factor (BDNF). HPRT1 was used as the control gene.

Figure 18:
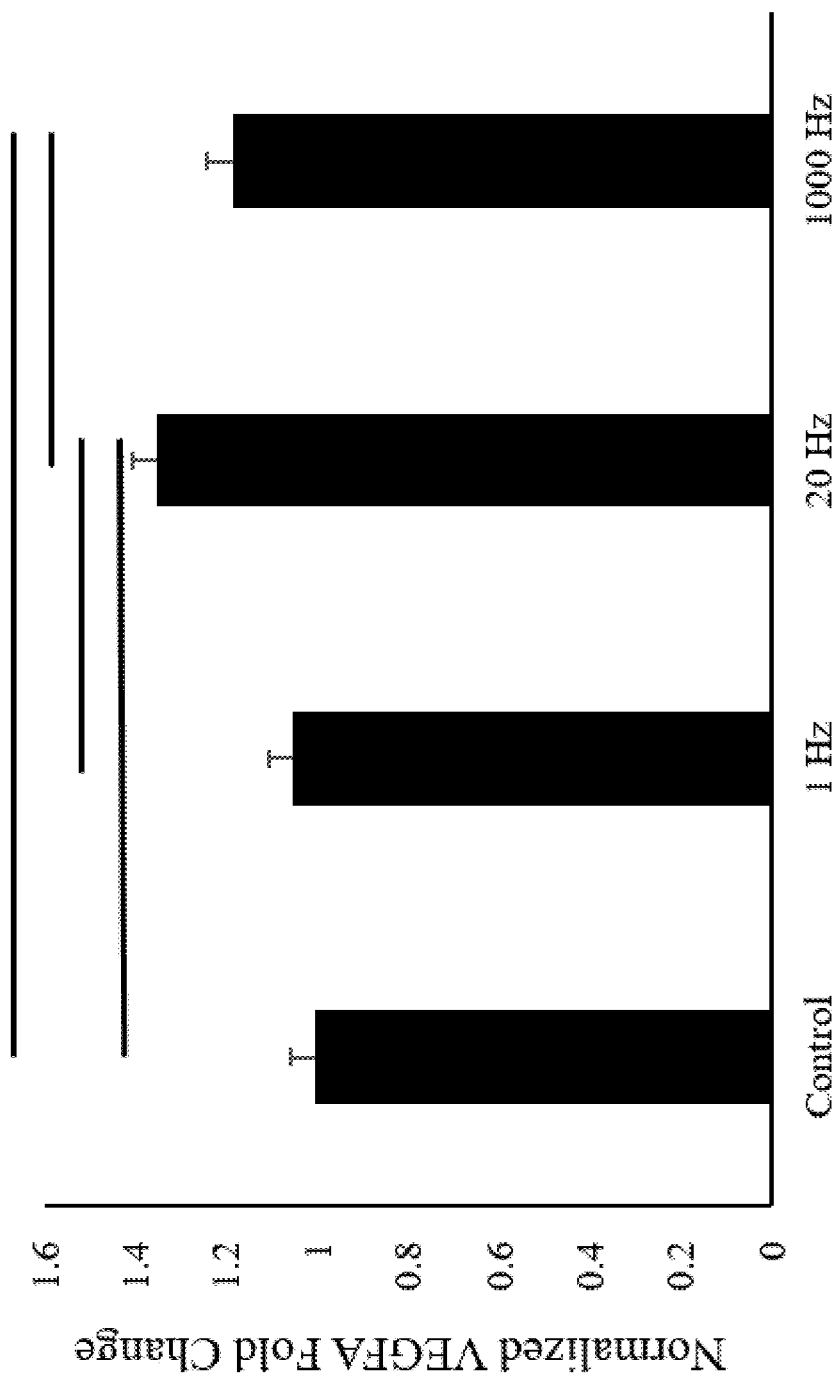
FIG. 18 shows gene expression analysis of VEGFA in ASC lysates after 0, 1 Hz, 20 Hz, or 1000 Hz E-stim. Bar indicates p-value<0.05.
Figure 19:
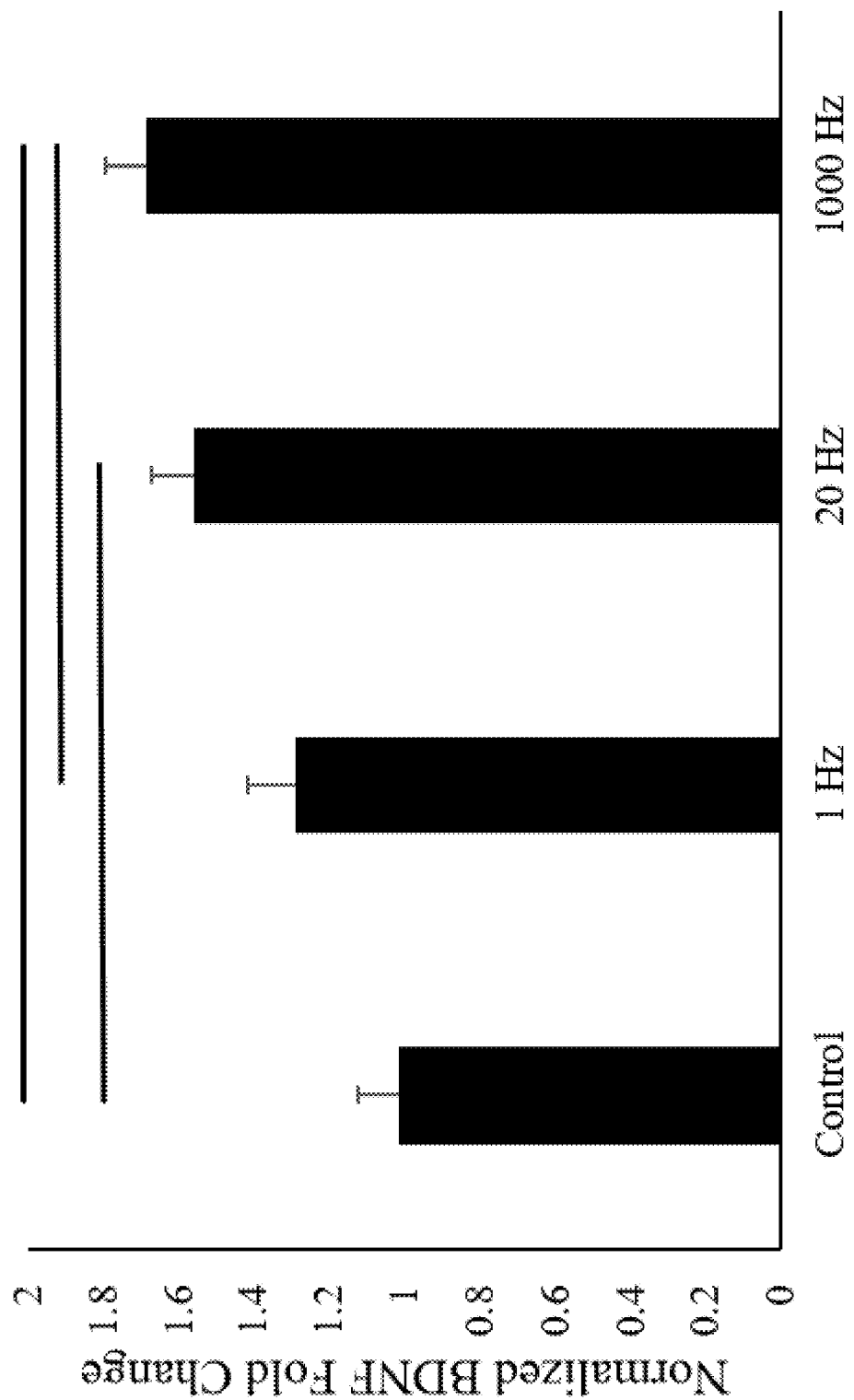
FIG. 19 shows gene expression analysis of BDNF in ASC lysates after 0, 1 Hz, 20 Hz, or 1000 Hz E-stim. Bar indicates p-value<0.05.

20 Hz elicited the highest expression of VEGFA, which is indicative of wound healing applications (FIG. 18). 1000 Hz elicited the heights expression of BDNF, which is indicative of neural repair applications (FIG. 19).

Figure 20:
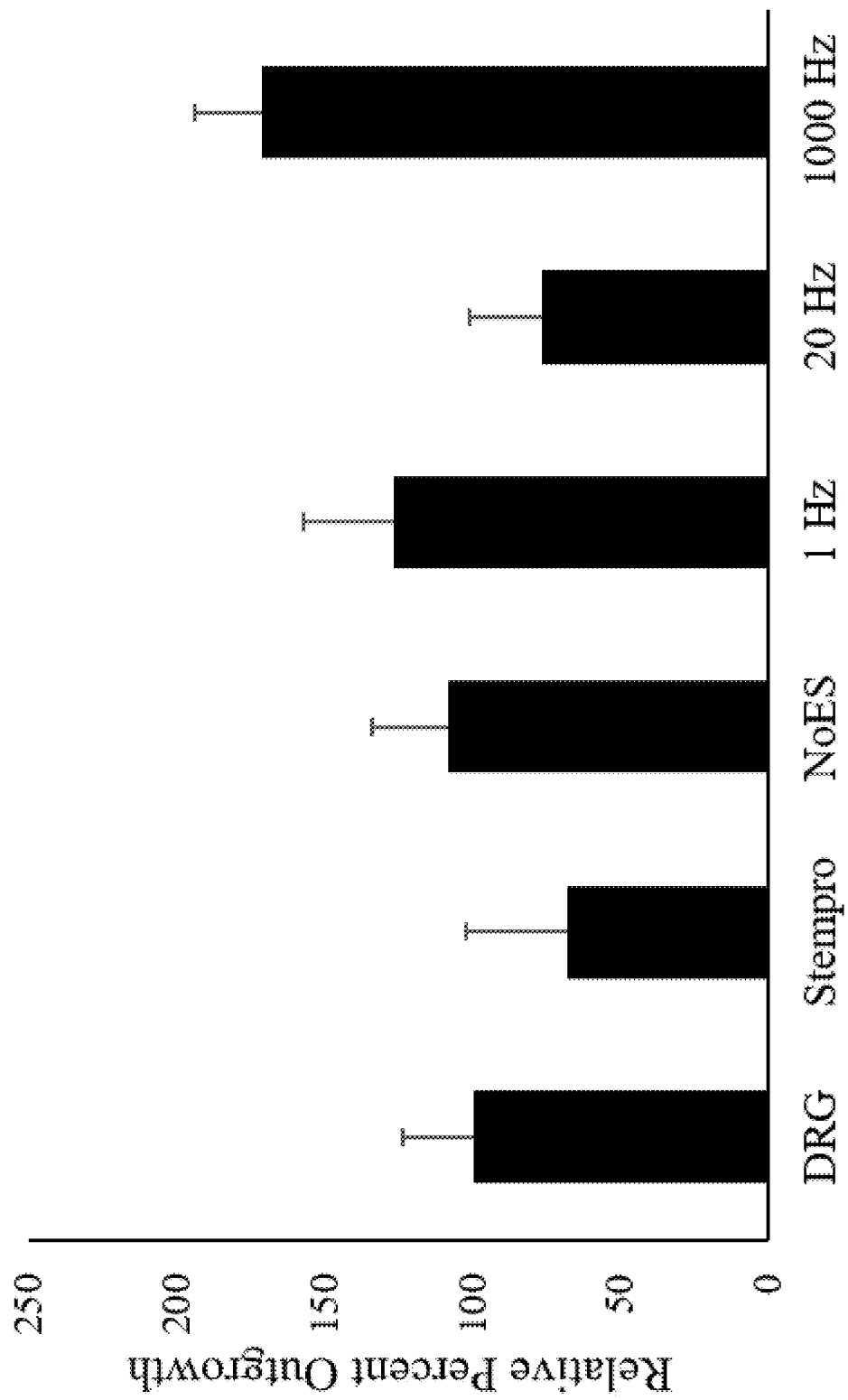
FIG. 20 shows dorsal root ganglia (DRG) outgrowth after 3 days culture with secretome from ASCs treated with Stempro, 0 Hz, 1 Hz, 20 Hz, or 1000 Hz E-stim.

To test the effect of E-stim on neural repair applications, dorsal root ganglia (DRG) were isolated and cultured for 3 days with secretome from different ASC stimulation regimes. DRG outgrowth was quantified as a change in area of outgrowth from the body of the DRG. 1000 Hz elicited higher outgrowth compared to other groups (FIG. 20).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a human having a spinal cord injury, consisting of administering to the human in need thereof a composition consisting essentially of a secretome derived from electrically stimulated cells in a therapeutically effective amount to treat the spinal cord injury in the human in need thereof, wherein the cells have been electrically stimulated in an electrical field of from about 20 V/m to about 50 V/m.

2. The method of claim 1, wherein the cells are adipose derived stem cells (ASCs) or Schwann cells.

3. The method of claim 1, wherein the cells are autologous cells isolated from the human.

4. The method of claim 1, wherein the secretome is produced by a process consisting essentially of collecting cells from the human, culturing the cells in a serum free medium for at least one day while stimulating the cells with electric pulses, and collecting the secretome produced by the electrically-stimulated cells.

5. The method of claim 1, wherein the electrical pulses have a frequency from 1 Hz to 1000 Hz.

6. The method of claim 1, wherein the composition is an injectable hydrogel of the secretome.

7. The method of claim 1, wherein the cells are electrically stimulated using platinum electrodes.

* * * * *